US011125741B2

(12) United States Patent
Que et al.

(10) Patent No.: US 11,125,741 B2
(45) Date of Patent: *Sep. 21, 2021

(54) COMPOSITIONS AND METHODS FOR THE DETECTION OF ZINC

(71) Applicant: Northwestern University, Evanston, IL (US)

(72) Inventors: Emily L. Que, Chicago, IL (US); Thomas V. O'Halloran, Chicago, IL (US); Teresa K. Woodruff, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/899,543

(22) Filed: Feb. 20, 2018

(65) Prior Publication Data

US 2019/0033299 A1 Jan. 31, 2019

Related U.S. Application Data

(63) Continuation of application No. 14/503,914, filed on Oct. 1, 2014, now Pat. No. 9,897,595, which is a continuation of application No. 14/078,743, filed on Nov. 13, 2013, now abandoned, said application No. 14/503,914 is a continuation-in-part of application No. 13/442,453, filed on Apr. 9, 2012, now abandoned.

(60) Provisional application No. 61/726,845, filed on Nov. 15, 2012.

(51) Int. Cl.
| | |
|---|---|
| *A61K 31/40* | (2006.01) |
| *A61K 31/69* | (2006.01) |
| *G01N 33/52* | (2006.01) |
| *A61K 31/435* | (2006.01) |
| *G01N 31/22* | (2006.01) |
| *G01N 33/84* | (2006.01) |
| *G01N 33/50* | (2006.01) |
| *C07F 5/02* | (2006.01) |

(52) U.S. Cl.
CPC ............ *G01N 33/52* (2013.01); *A61K 31/40* (2013.01); *A61K 31/435* (2013.01); *A61K 31/69* (2013.01); *C07F 5/022* (2013.01); *G01N 31/22* (2013.01); *G01N 33/5091* (2013.01); *G01N 33/84* (2013.01)

(58) Field of Classification Search
CPC ....... A61K 31/40; A61K 31/435; A61K 31/69
See application file for complete search history.

(56) References Cited

U.S. PATENT DOCUMENTS

| | | |
|---|---|---|
| 7,105,680 B1 | 9/2006 | O'Halloran et al. |
| 9,897,595 B2 | 2/2018 | Que et al. |
| 2001/0009762 A1 | 7/2001 | Ach |
| 2009/0181364 A1 | 7/2009 | Gee |
| 2012/0271100 A1 | 10/2012 | Woodruff et al. |
| 2014/0134665 A1 | 5/2014 | Que et al. |

FOREIGN PATENT DOCUMENTS

| | | |
|---|---|---|
| WO | 1993/006868 | 4/1993 |
| WO | 1994/008629 | 4/1994 |
| WO | 1994/009056 | 4/1994 |
| WO | 1996/026754 | 9/1996 |

OTHER PUBLICATIONS

Battaglia et al. "Influence of the calcium ionophore A23187 on rat egg behavior and cortical F-actin," Gamete Res, 1987, 18, 141-52.
Bernhardt et al. "Zinc requirement during meiosis I-meiosis II transition in mouse oocytes is independent of the MOS-MAPK pathway," Biol Reprod, 2011, 84: 526-536.
Berridge et al. "Calcium signalling: dynamics, homeostasis and remodelling," Nat Rev Mol Cell Biol, 2003, 4, 517-29.
Dimaggio et al. "Cortical granule exocytosis in hamster eggs requires microfilaments," Mol Reprod Dev, 1997, 47, 334-40.
Domaille et al. "Visualizing ascorbate-triggered release of labile copper within living cells using a ratiometric fluorescent sensor," J. Am. Chem. Soc 2010, 132, 1194-1195.
Ducibella et al. "Egg-to-embryo transition is driven by differential responses to Ca(2+) oscillation number," Dev Biol, 2002, 250, 280-91.
Ducibella, T. "The cortical reaction and development of activation competence in mammalian oocytes," Hum Reprod Update, 1996, 2, 29-42.
Duncan et al. "PAR-3 defines a central subdomain of the cortical actin cap in mouse eggs," Dev Biol, 2005, 280, 38-47.
Fahrni et al. "Aqueous coordination chemistry of quinolinebased fluorescence probes for the biological chemistry of zinc," J Am Chem Soc, 1999, 121, 11448-11458.
Gee et al. "Detection and imaging of zinc secretion from pancreatic beta-cells using a new fluorescent zinc indicator," J Am Chem Soc, 2002, 124, 776-8.
Grynkiewicz et al. "A new generation of Ca2+ indicators with greatly improved fluorescence properties," J Biol Chem, 1985, 260, 3440-50.
Haugland, H. P., "Handbook of fluorescent probes and research chemicals." 6th ed.; Molecular Probes: Eugene, OR, 2001; Bookcopy not provided.
Hureau, et al. "Syntheses, X-ray structures, solid state high-field electron paramagnetic resonance, and density-functional theory investigations on chloro and aqua Mn(II) mononuclear complexes with amino-pyridine pentadentate ligands," Inorg. Chem. 2008, 47, 9238-9247.

(Continued)

*Primary Examiner* — Yong S. Chong
(74) *Attorney, Agent, or Firm* — Casimir Jones, S.C.; Jason R. Bond

(57) ABSTRACT

The invention relates generally to compositions and methods for the detection of zinc. In particular, compositions and methods are provided to detect changes in cellular zinc concentration and to correlate them to cellular phenomena.

5 Claims, 29 Drawing Sheets

(56) References Cited

OTHER PUBLICATIONS

Kim et al. "Zinc availability regulates exit from meiosis in maturing mammalian oocytes," Nat Chem Biol, 2010, 6, 674-81.

Kline et al. "Repetitive calcium transients and the role of calcium in exocytosis and cell cycle activation in the mouse egg," Dev Biol, 1992, 149, 80-9.

Kramer, C. Y. "Extension of multiple range tests to group means with unequal numbers of replications," Biometrics, 1956, 12, 309-310.

Kubiak, J. Z. "Mouse oocytes gradually develop the capacity for activation during the metaphase II arrest," Dev Biol, 1989, 136, 537-45.

Lawrence et al. "Sperm-egg fusion is the prelude to the initial Ca2+ increase at fertilization in the mouse," Development, 1997, 124, 233-41.

Liu et al. "Calcium elevation at fertilization coordinates phosphorylation of XErp1/Emi2 by Plx1 and CaMK II to release metaphase arrest by cytostatic factor," Curr Biol, 2005, 15, 1458-68.

Longo et al. "Development of cortical polarity in mouse eggs: involvement of the meiotic apparatus," Dev Biol, 1985, 107, 382-94.

Madgwick et al. "Mouse Emi2 is required to enter meiosis II by reestablishing cyclin B1 during interkinesis," J Cell Biol, 2006, 174, 791-801.

Markoulaki et al. "Oscillatory CaMKII activity in mouse egg activation," Dev Biol, 2003, 258, 464-74.

Ozil et al. "Ca2+ oscillatory pattern in fertilized mouse eggs affects gene expression and development to term," Dev Biol, 2006, 300, 534-44.

Ozil, J. P. "The parthenogenetic development of rabbit oocytes after repetitive pulsatile electrical stimulation," Development, 1990, 109, 117-27.

Shoji et al. "Mammalian Emi2 mediates cytostatic arrest and transduces the signal for meiotic exit via Cdc20," EMBO J, 2006, 25, 834-45.

Stork et al. "Intracellular zinc elevation measured with a "calciumspecific" indicator during ischemia and reperfusion in rat hippocampus: a question on calcium overload," J Neurosci, 2006, 26, 10430-7.

Suzuki et al. "Full-term mouse development by abolishing Zn2+-dependent metaphase II arrest without Ca2+ release," Development, 2010, 137, 2659-2669.

Suzuki et al. "Mouse Emi2 as a distinctive regulatory hub in second meiotic metaphase," Development, 2010, 137, 3281-91.

Tahara et al. "Dynamics of cortical granule exocytosis at fertilization in living mouse eggs," Am J Physiol, 1996, 270, C1354-61.

Taki et al. "Emission ratiometric imaging of intracellular zinc: design of a benzoxazole fluorescent sensor and its application in two-photon microscopy," J Am Chem Soc, 2004, 126, 712-3.

Tingen et al. "Research funding. Politics and parthenotes," Science, 2010, 330, 453.

Tomalia et al., "Starburst Dendrimers: Molecular-Level Control of Size, Shape, Surface Chemistry, Topology, and Flexibility from Atoms to Macroscopic Matter," Angew. Chem. Int. Ed. Engl., 1990, 29: 138-175.

Toth et al. "Egg activation is the result of calcium signal summation in the mouse," Reproduction, 2006, 131, 27-34.

Wong et al. "Membrane hemifusion is a stable intermediate of exocytosis," Dev Cell 12, 2007, 653-9.

Xu et al. "Identification of a stage-specific permissive in vitro culture environment for follicle growth and oocyte development," Biol Reprod, 2006, 75, 916-23.

Zernicka-Goetz, M. "Spontaneous and induced activation of rat oocytes," Mol Reprod Dev, 1991, 28, 169-76.

Zhang et al. "Strontium promotes calcium oscillations in mouse meiotic oocytes and early embryos through InsP3 receptors, and requires activation of phospholipase and the synergistic action of InsP3," Hum Reprod, 2005, 20, 3053-61.

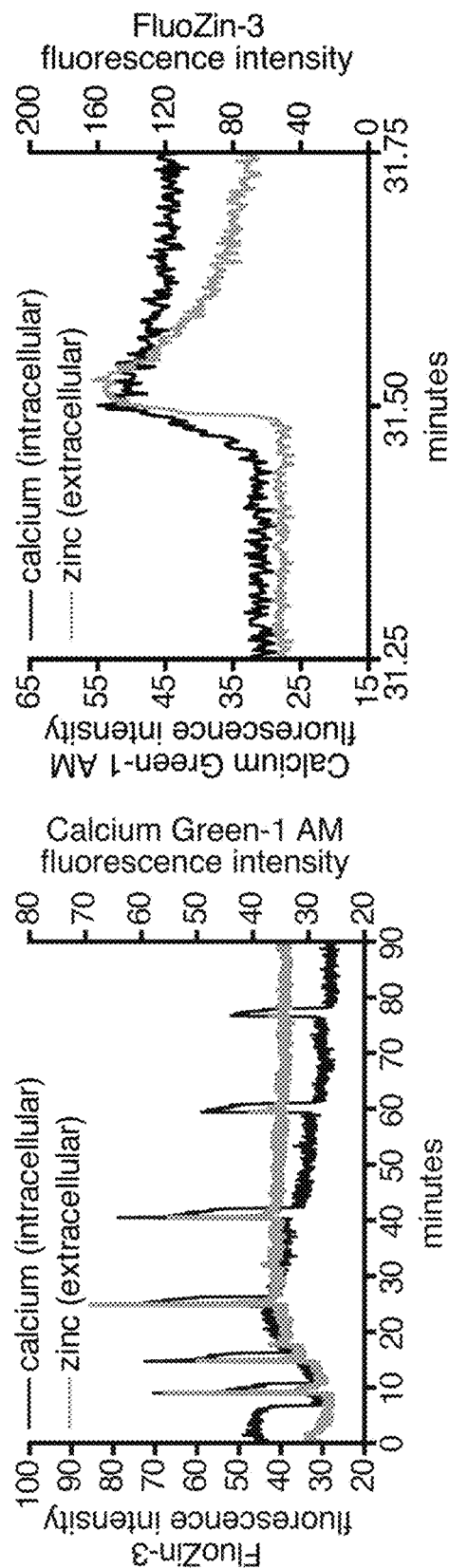

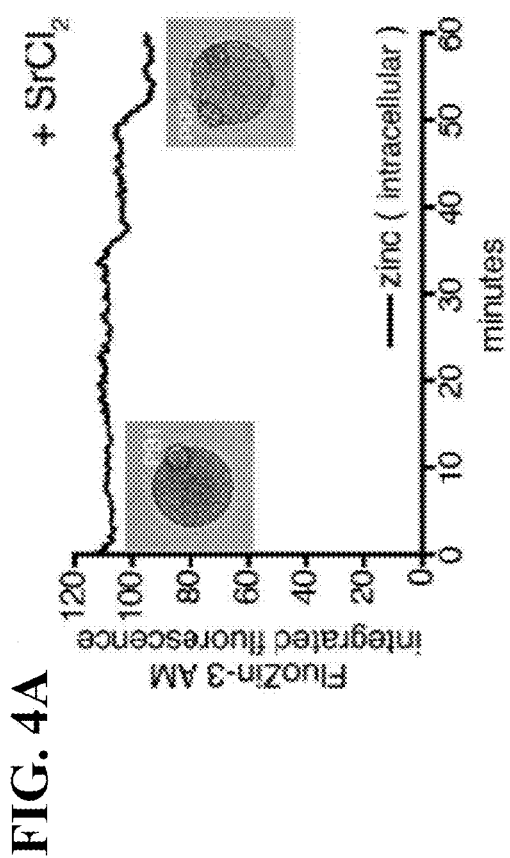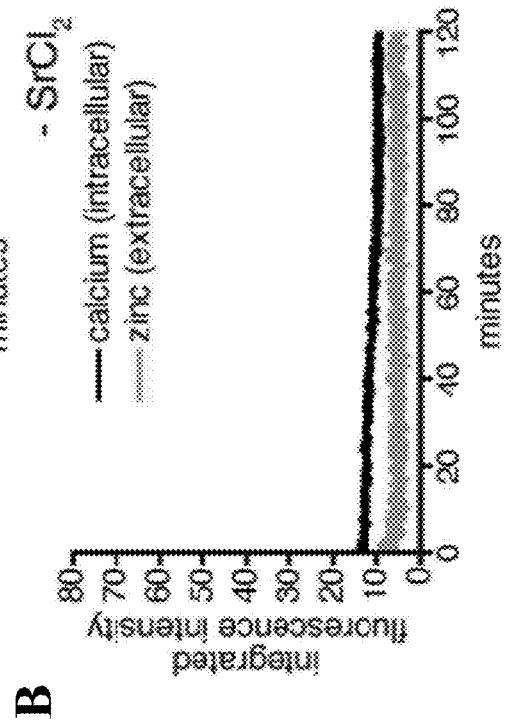
FIG. 4A
FIG. 4B

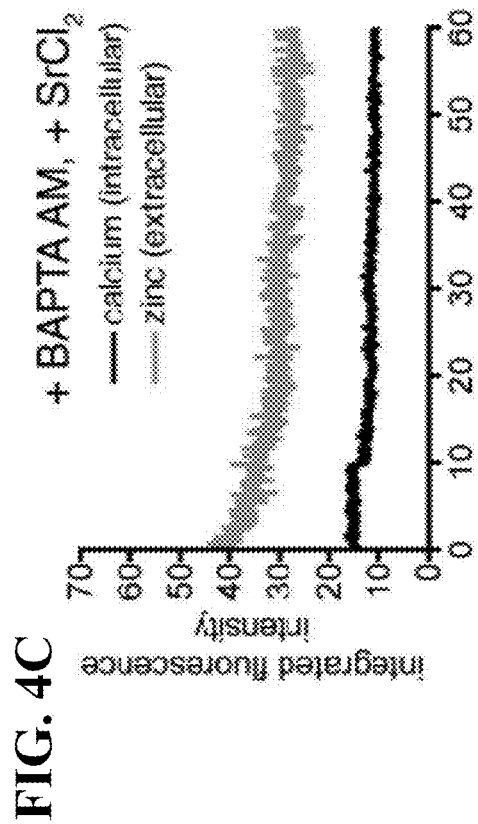
FIG. 4C
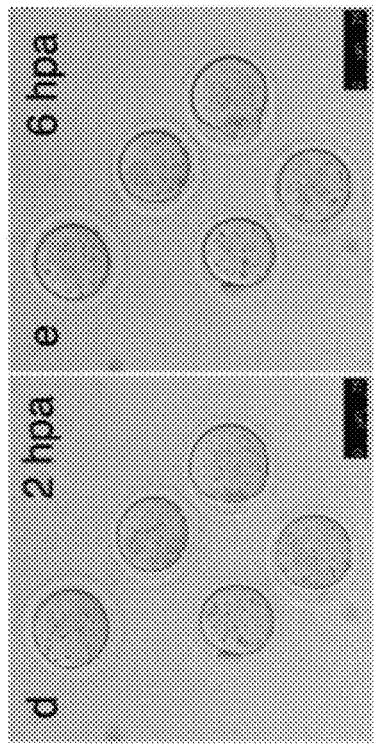
FIG. 4D
FIG. 4E

FIG. 7
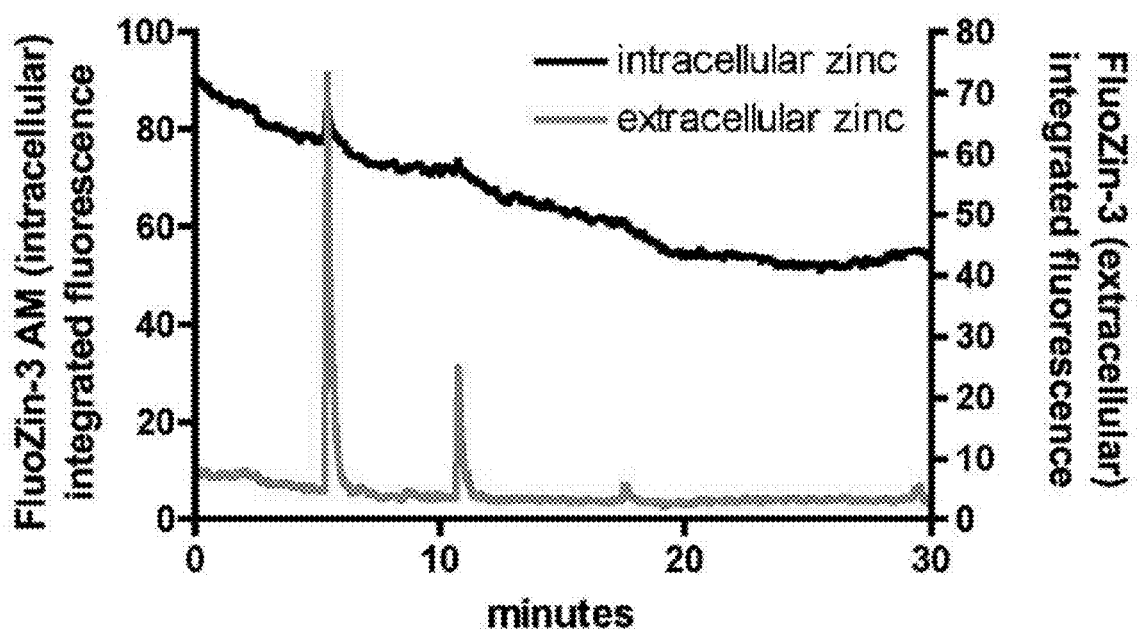
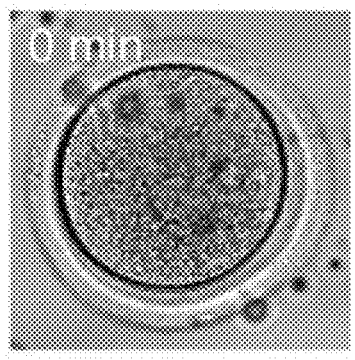
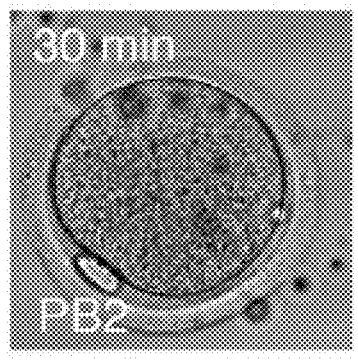
brightfield

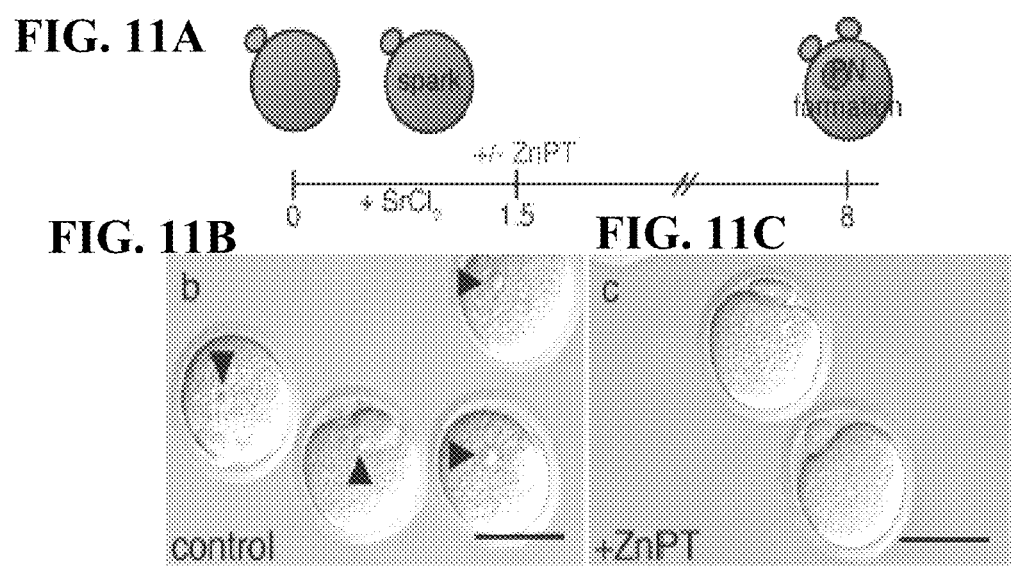

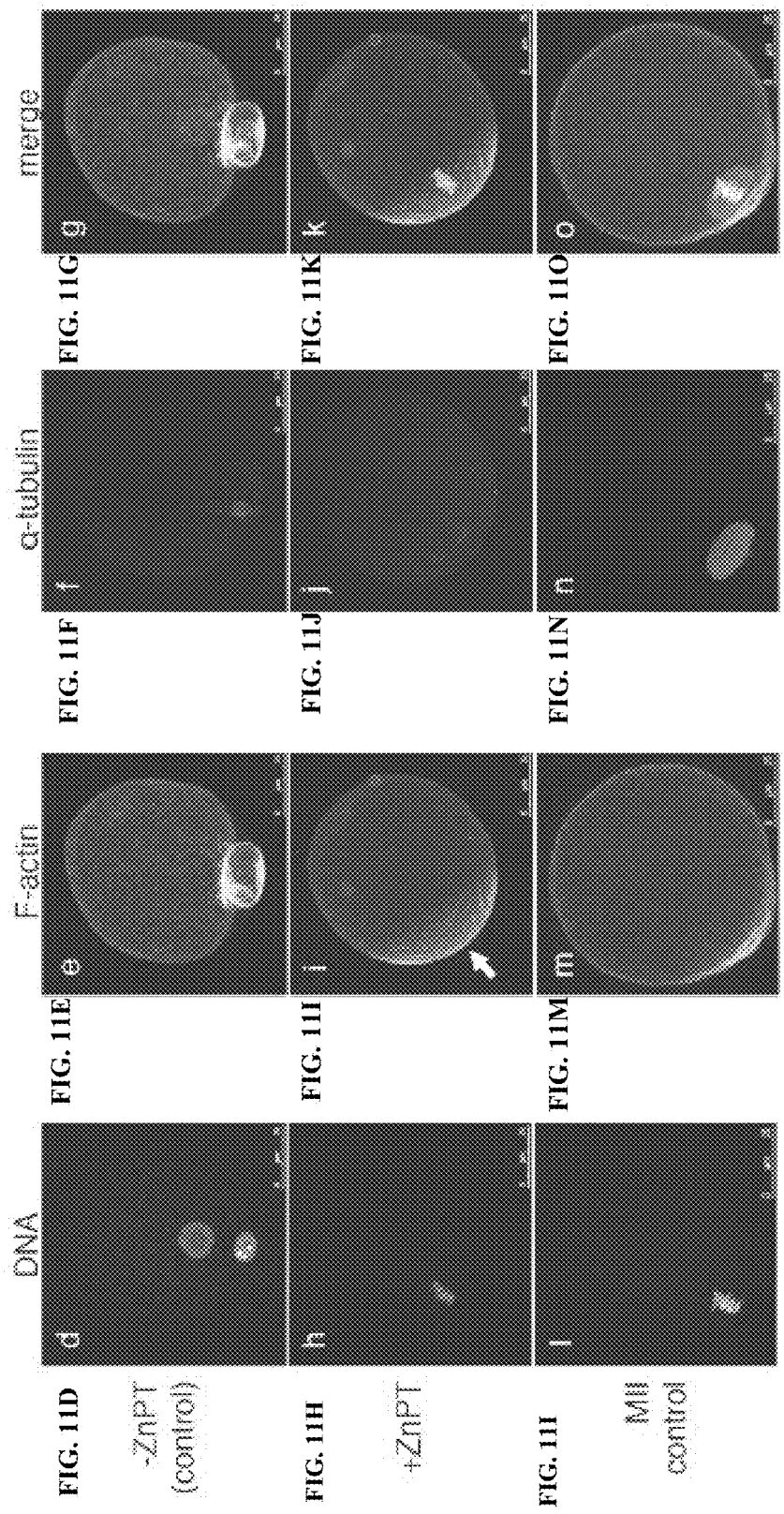

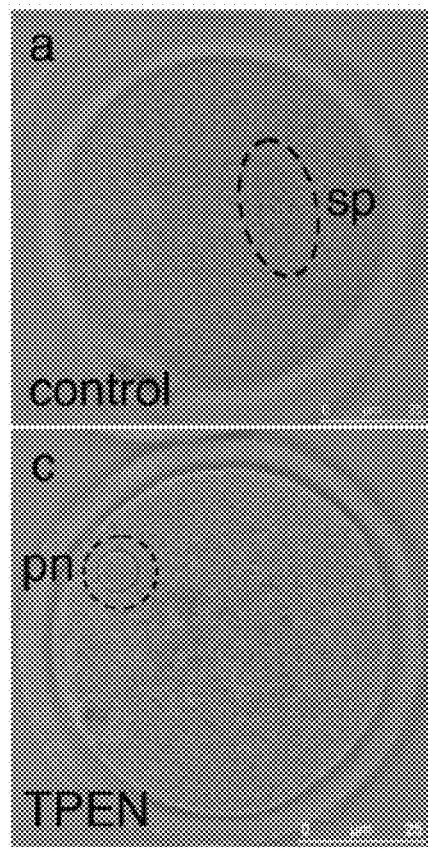
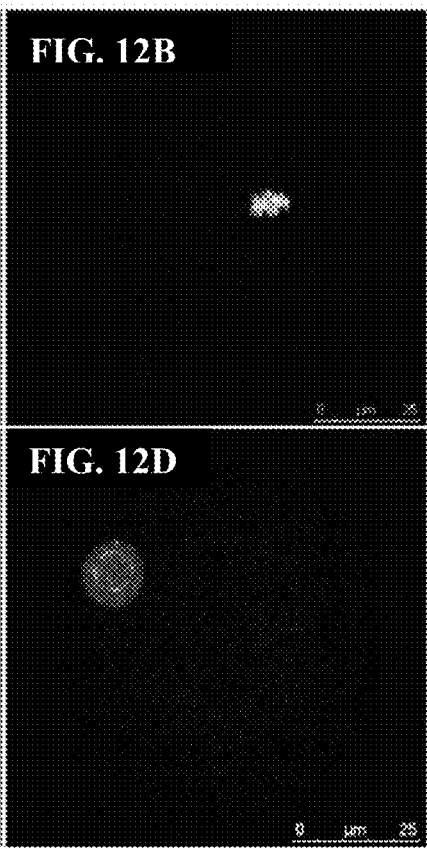
FIG. 12A　FIG. 12B
FIG. 12C　FIG. 12D
FIG. 12E
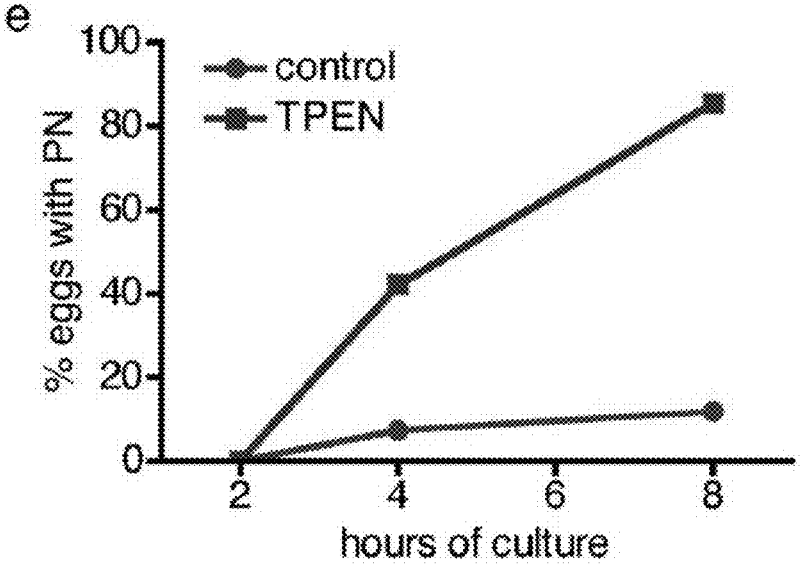

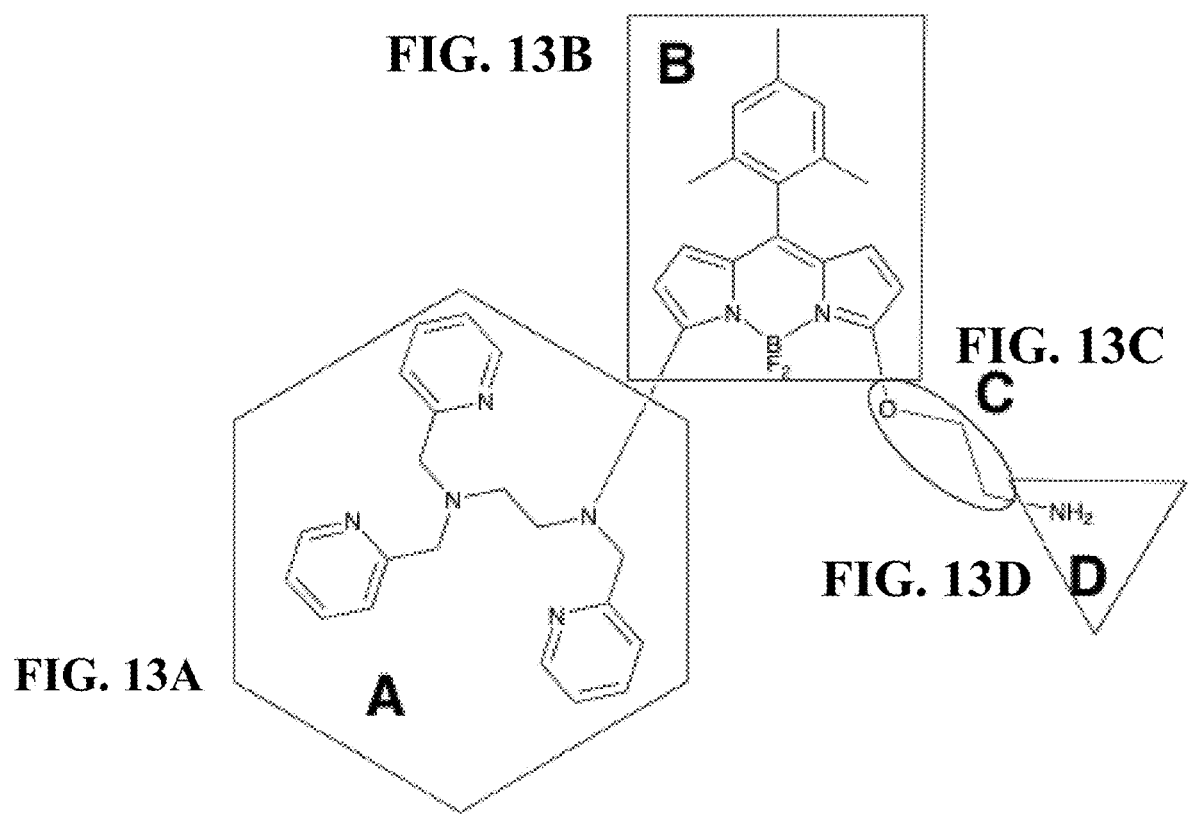

FIG. 22
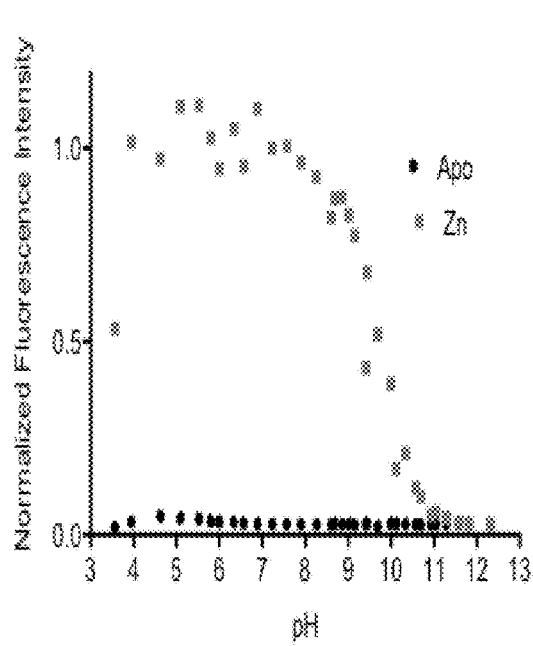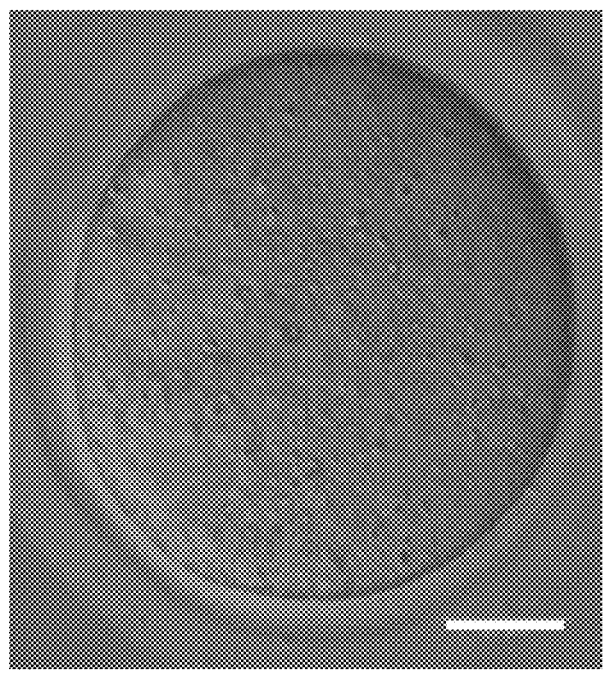

COMPOSITIONS AND METHODS FOR THE DETECTION OF ZINC

CROSS-REFERENCE TO RELATED APPLICATIONS

The present invention is a continuation of U.S. patent application Ser. No. 14/503,914, filed Oct. 1, 2014, which a continuation of Ser. No. 14/078,743, filed Nov. 13, 2013, now abandoned, which claims priority to U.S. Provisional Patent Application 61/726,845, filed Nov. 15, 2012; and a continuation-in-part of U.S. patent application Ser. No. 13/442,453, filed Apr. 9, 2012, now abandoned, each of which is incorporated by reference in its entirety.

STATEMENT REGARDING FEDERALLY SPONSORED RESEARCH OR DEVELOPMENT

This invention was made with government support under GM038784 and P01 HD021921 awarded by the National Institutes of Health. The government has certain rights in the invention.

FIELD OF THE INVENTION

The invention relates generally to compositions and methods for the detection of zinc. In particular, compositions and methods are provided to detect physiological changes in zinc concentration (e.g., extracellular, intracellular, etc.) and to correlate them to cellular phenomena.

BACKGROUND OF THE INVENTION

The biological functions of metal ions have traditionally been thought to be limited to structural and catalytic roles within proteins. However, metal ions are also known to play signaling roles at the cellular level. For example, the alkaline earth metal calcium is one metal in which biological signaling roles are particularly well-established. Periodic elevations in the intracellular concentration of free calcium ions, also known as calcium transients or oscillations, are readily detected using fluorescent probes and are known to drive a number of biological processes (Berridge et al. (2003) *Nat Rev Mol* Cell *Biol* 4, 517-29.; herein incorporated by reference in its entirety). This is perhaps best illustrated in the egg, where repetitive calcium transients are among the earliest observable events after fertilization (Lawrence et al. (1997) Development 124, 233-41.; herein incorporated by reference in its entirety). Several parameters of these calcium transients, including total number, frequency, and amplitude influence which downstream developmental events are initiated (Ozil et al. (2006) *Dev Biol* 300, 534-44.; Ducibella et al. (2002) *Dev Biol* 250, 280-91.; Toth et al. (2006) Reproduction 131, 27-34.; herein incorporated by reference in their entireties). These cellular processes, which include cortical granule (CG) exocytosis and cell cycle progression can be initiated in the absence of sperm by stimulatory agents that induce parthenogenesis (Kline & Kline. (1992) *Dev Biol* 149, 80-9.; Tahara et al. (1996) Am J Physiol 270, C1354-61.; Liu & Maller. (2005) *Curr Biol* 15, 1458-68.; Madgwick et al. (2006) J Cell *Biol* 174, 791-801.; Battaglia & Gaddum-Rosse. (1987) *Gamete Res* 18, 141-52.; Ozil. (1990) Development 109, 117-27.; Zhang et al. (2005) *Hum Reprod* 20, 3053-61.; Tingen (2010) Science 330, 453; herein incorporated by reference in their entireties). Interestingly, the normal pattern of calcium oscillations is disrupted in eggs matured under conditions which limit the availability of the transition metal zinc (Kim et al. (2010) *Nat Chem Biol* 6, 674-81.; herein incorporated by reference in its entirety), suggesting that the physiologies of these metals are somehow connected in the egg.

In a departure from its well-established role as an enzymatic cofactor or structure stabilizing agent, fluctuations in the total concentration of intracellular zinc have recently been shown to contribute to the proper cell cycle regulation in maturing oocytes. Intracellular zinc levels increase by more than fifty percent and over $10^{10}$ ions per cell are accrued during the final stage of oocyte maturation, also known as meiotic maturation (Kim et al. (2010) Zinc availability regulates exit from meiosis in maturing mammalian oocytes, *Nat Chem Biol* 6, 674-81.; herein incorporated by reference in its entirety). This significant cellular metal accumulation event occurs over a remarkably short time interval and is a physiological imperative, as insufficient accumulation of zinc leads to a premature meiotic arrest at telophase I instead of metaphase II (Kim et al. (2010) *Nat Chem Biol* 6, 674-81.). This zinc-dependent meiotic checkpoint arises, in part, because zinc-insufficient eggs fail to reestablish maturation promoting factor (MPF) activity (Bernhardt et al. (2010) *Biol Reprod*, published ahead of print Nov. 10, 2010.; herein incorporated by reference in its entirety), which is necessary for eggs to set up and maintain meiotic arrest at metaphase II.

SUMMARY OF THE INVENTION

In some embodiments, the present invention provides a Zn-responsive probe comprising: (a) a Zn-binding group configured to coordinate one or more Zn ions; (b) a signaling moiety configured to emit a detectable signal; and (c) an attachment group, wherein said attachment group is a chemically reactive with one or more functional groups. In some embodiments, the detectable signal of the signaling moiety is altered by coordination of one or more Zn ions by the Zn-binding moiety. In some embodiments, the signaling moiety comprises a fluorophore. In some embodiments, the fluorescence intensity, emission spectra, and/or excitation spectra of the signaling moiety is altered by coordination of one or more Zn ions by the Zn-binding moiety. In some embodiments, the interaction of the attachment group with a chemically reactive functional group results in covalent or stable non-covalent attachment of the Zn-responsive probe to the functional group. In some embodiments, the Zn-binding group is attached to the signaling group, and the signaling group is attached to the attachment group. In some embodiments, the one or more attachments are though a linker group. In some embodiments, the functional group is attached to a surface.

In some embodiments, the present invention provides a method of non-invasively detecting Zn release and/or uptake by a cell or cells comprising: (a) contacting a sample comprising a cell or cells with a Zn-responsive probe (e.g., a Zn-responsive probe attached to a solid surface); (b) detecting the signal emitted by the signaling moiety over time; and (c) correlating signal emitted with Zn concentration (e.g., intracellular or extracellular). In some embodiments, the sample comprises one or more oocytes (e.g., human oocytes (e.g., for use in in vitro fertilization), non-human oocyctes (e.g., oocytes of a non-human primate, domestic animal (e.g., feline, canine, etc.), agricultural animal (e.g., bovine, porcine, etc.)). In some embodiments, the present invention further comprises (d) removing the sample from the Zn-responsive probe (e.g. separating the cell and the Zn-responsive probe). In some embodiments, removing the sample from the Zn-responsive probe (or the Zn-responsive probe from the sample) is facilitated by the attachment of the probe to a solid surface.

In some embodiments, the present invention provides a method of detecting the fertilization of an oocyte comprising: (a) contacting a sample comprising an metaphase-II-arrested oocyte with a Zn-responsive probe (e.g., a Zn-responsive probe attached to a solid surface); (b) contacting the sample with sperm; (c) detecting a significant increase in extracellular Zn concentration based on a change in the signal of the Zn-responsive probe; and (d) correlating the significant increase in extracellular Zn concentration to fertilization of the oocyte by the sperm. In some embodiments, methods further comprise (f) removing the oocyte from the Zn-responsive probe; and (g) implanting the fertilized oocyte into a subject. In some embodiments, the Zn-responsive probe is attached to a surface. In some embodiments, removing the oocyte from the Zn-responsive probe is facilitated by the attachment of the probe to a surface. In some embodiments, attachment of the Zn-responsive probe to a surface prevents uptake of the probe into the oocyte.

In some embodiments, the present invention provides a method of evaluating the quality of an oocyte for fertilization comprising: (a) contacting a surface with a sample comprising the oocyte, wherein said surface displays a plurality of Zn-responsive probes (e.g., Zn-responsive probes are attached to the surface); (b) detecting the signal emitted by the Zn-responsive probes over time; (c) correlating the signal emitted with extracellular Zn concentration, wherein a decrease in extracellular Zn is indicative of an oocyte that is ready for fertilization. In some embodiments, the oocyte is in prophase-I-arrest upon contacting with the surface. In some embodiments, methods further comprise (d) removing the oocyte from the Zn-responsive probe. In some embodiments, removing the oocyte from the Zn-responsive probe is facilitated by the attachment of the probe to a surface. In some embodiments, attachment of the Zn-responsive probe to a surface prevents uptake of the probe into the oocyte.

In some embodiments, the present invention provides compositions comprising a solid surface displaying one or more Zn-responsive probes, wherein said Zn-responsive probes comprise: (a) a Zn-binding group configured to coordinate one or more Zn ions; and (b) a signaling moiety configured to emit a detectable signal. In some embodiments, the detectable signal of the signaling moiety is altered by coordination of one or more Zn ions by the Zn-binding moiety. In some embodiments, the signaling moiety comprises a fluorophore. In some embodiments, the fluorescence intensity, emission spectrum, and/or excitation spectrum of the signaling moiety is altered by coordination of one or more Zn ions by the Zn-binding moiety. In some embodiments, the composition further comprises a linker. In some embodiments, the linker connects the Zn-binding group with the signaling moiety. In some embodiments, the linker connects the Zn-binding group and/or the signaling moiety to the solid surface. In some embodiments, the Zn-responsive probes are attached to the solid surface through the interaction of a attachment group on the Zn-responsive probe and an anchor moiety on the solid surface. In some embodiments, the solid surface is selected from the group comprising: a plate, bead, well, slide, biopolymer, cell surface, and tube.

In some embodiments, the present invention provides a method for detection of Zn in a sample (e.g., by any suitable method). In some embodiments, a change in Zn concentration is detected. In some embodiment, Zn is detected by a Zn-responsive probe. In some embodiments, Zn is detected without a probe. In some embodiments, detection of Zn is correlated to a biological function or process (e.g., oocyte fertilization). In some embodiments, a Zn-responsive probe is attached to a solid surface (e.g., bead, plate, slide, well, etc.). In some embodiments, attachment of a Zn-responsive probe to a solid surface facilitates removal of the probe from a sample without contaminating the sample with Zn-responsive probe. In some embodiments, attachment of a Zn-responsive probe to a solid surface facilitates removal of the sample from a surface (e.g., (tube, well, slide, etc.) without contaminating the sample with Zn-responsive probe. In some embodiments, attachment of the Zn-responsive probe to a surface prevents uptake of the probe into the sample.

In certain embodiments, the present invention provides a Zn-responsive probe which has the following chemical structure:

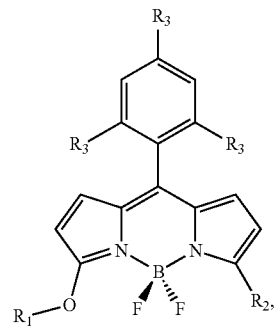

wherein each of said $R_{3s}$ are individually selected from: H, $CH_3$, an alkyl group, an O-alkyl group, an N-alkyl group, a linker group, an attachment group, and a linker group attached to an attachment group; wherein said $R_1$ is selected from: H, $CH_3$, an alkyl group, a linker group, an attachment group, and a linker group attached to an attachment group; and wherein said $R_2$ is a Zn binding group.

In some embodiments, the Zn binding group has the following formula:

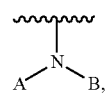

wherein A and B each seperately comprise at least one moiety selected from an amine donor, an oxygen donor, and a sulfur donor.

In further embodiment, the Zn binding group has the following formula:

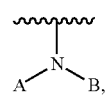

wherein A and B each seperately comprise at least one moiety selected from a pyridine, an amine, an imidazole, a sulfonamide, a carboxylate, a phenol, an ether, an alcohol, a thiol, a thioether, and a thiophene.

In particular embodiments, the Zn binding group has the following formula:

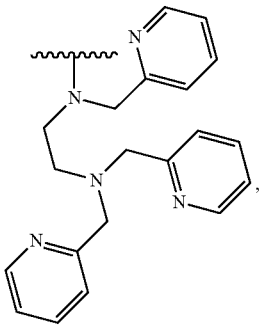 [SMILES: *N(CCN(Cc1ccccn1)Cc1ccccn1)Cc1ccccn1]

or a derivative of said formula that is able to chelate zinc.

In other embodiments, the Zn-responsive probe has the following chemical structure:

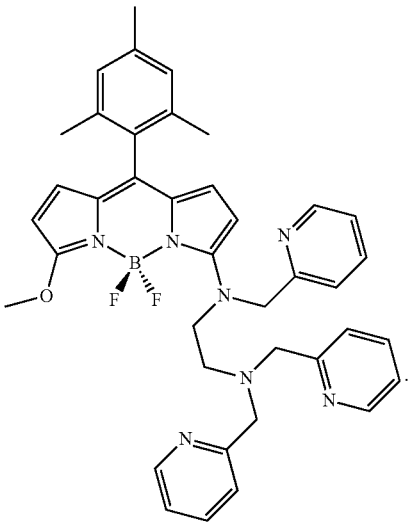

In some embodiments, each of the $R_{3s}$ are methyl groups. In other embodiments, each of the $R_{3s}$ are either hydrogen or an alkyl group. In further embodiments, $R_1$ is a methyl group or hydrogen. In further embodiments, $R_1$ and/or $R_3$ is an attachment group. In further embodiments, $R_1$ and/or $R_3$ is a linker attached to an attachment group.

In particular embodiments, the present invention provides methods of non-invasively detecting Zn release and/or uptake by a cell or cells comprising: a) contacting a sample comprising a cell or cells with a composition comprising a Zn-responsive probe, wherein the Zn-responsive probe is present in said composition at a concentration between $1 \times 10^{-5}$ M and $1 \times 10^{-9}$ M; b) detecting the signal emitted by the signaling moiety over time; and c) correlating signal emitted with Zn concentration.

In certain embodiments, the sample comprises one or more oocytes. In other embodiments, the Zn-responsive probe is attached to a surface. In particular embodiments, the concentration of the Zn-responsive probe is between $1 \times 10^{-7}$ M and $9 \times 10^{-8}$ M. In further embodiments, the cell comprises a metaphase-II-arrested oocyte, wherein the method further comprises a step before step b) of contacting the sample with sperm, and wherein the detecting the signal comprises detecting a significant increase in extracellular Zn concentration based on a change in the signal of the Zn-responsive probe. In further embodiments, the correlating the signal comprises correlating the significant increase in extracellular Zn concentration to fertilization of the oocyte by the sperm. In other embodiments, the methods further comprise removing the oocyte from the Zn-responsive probe, and implanting the fertilized oocyte into a subject. In particular embodiments, the Zn-responsive probe has one of the chemical structures shown above or in the figures.

In some embodiments, the present invention provides methods of evaluating the quality of an oocyte for fertilization comprising: a) contacting a surface with a sample comprising the oocyte, wherein said surface displays a plurality of Zn-responsive probes; b) detecting the signal emitted by the Zn-responsive probes over time; and c) correlating the signal emitted with extracellular Zn concentration, wherein a decrease in extracellular Zn is indicative of an oocyte that is ready for fertilization.

In certain embodiments, the oocyte is in prophase-I-arrest upon contacting with the surface. In other embodiments, the Zn-responsive probe is attached to a surface. In additional embodiments, the Zn-responsive probe has one of the chemical structures shown above or in the figures.

In particular embodiments, the present invention provides methods of non-invasively detecting Zn release and/or uptake by a cell or cells comprising: a) contacting a sample comprising a cell or cells with a composition comprising a Zn-responsive probe with the chemical structure recited above or in the figures; b) detecting the signal emitted by the signaling moiety over time; and c) correlating signal emitted with Zn concentration.

In certain embodiments, the Zn-responsive probes describes herein are used to detect or label zinc in cells as part of flow cytometry type analyses. In particular embodiments, the Zn-responsive probes are used for extracellular zinc tracking, such as for monitoring zinc exocytosis. In certain embodiments, the Zn-responsive probes are used at concentrations to track zinc (e.g., inside biological samples) with minimal perturbation of normal physiology (e.g., at concentrations as low as $1 \times 10^{-7}$ M, $5 \times 10^{-7}$ M, $1 \times 10^{-8}$ M and $5 \times 10^{-8}$ M, or between $1 \times 10^{-7}$ and $9 \times 10^{-8}$ M.

BRIEF DESCRIPTION OF THE DRAWINGS

The description provided herein is better understood when read in conjunction with the accompanying drawings, which are included by way of example and not by way of limitation.

FIGS. 3a-c show that zinc sparks are polarized and are immediately preceded by intracellular calcium transients. Shortly following activation, zinc sparks occur around the egg cortex with the exception of a zinc spark-free region (a, 00:21:04, arrowhead). This spark-free region corresponds to the region containing the meiotic spindle, where the second polar body is extruded (a, 01:20:00, arrowhead). Egg activation was confirmed by simultaneously monitoring intracellular calcium oscillations with Calcium Green-1 AM every 4 s (b). Intracellular calcium increases immediately before a zinc spark, as evident when images were collected at a faster acquisition rate of every 100 ms in an independent experiment (c). Time is expressed as hh:mm:ss, wherein 00:00:00 represents the start of image acquisition. In all cases, extracellular zinc was detected with FluoZin-3.

FIGS. 4a-e show that zinc sparks did not occur in the absence of calcium transients. The membrane permeable derivative of FluoZin-3 (FluoZin-3 AM) did not detect intracellular oscillations in zinc (a), suggesting that those detected by Calcium Green-1 AM were specific to calcium. Insets are brightfield images taken at the beginning (left, first polar body denoted as PB1) and end (right) of the acquisition period. In each case, the presence of the second polar body (PB2) at the conclusion of imaging was observed, confirming successful egg activation and development. Zinc sparks were absent in the absence of an activating agent such as strontium chloride (b), or in eggs treated with the calcium-selective chelator BAPTA AM (c). Representative images illustrate that BAPTA AM-treated eggs neither extrude a second polar body (b, 2 hrs postactivation, or hpf) nor form a pronucleus (c, 6 hpf). Intracellular calcium was detected by Calcium Green-1 AM (black line) and extracellular zinc was detected by FluoZin-3 (gray line) in b and c. Scale bar=75 µm in d and e.

FIG. 7 shows intracellular zinc decreases in the activated egg. Corresponding to the onset of the zinc sparks (FluoZin-3, gray line), there is a gradual decrease in intracellular labile zinc that is detectable with a membrane-permeable zinc fluorophore (FluoZin-3 AM, black line). Successful egg activation and development was confirmed using simultaneous brightfield imaging, which revealed extrusion of a second polar body (PB2). The first (0 min, left) and final (30 min, right) brightfield images are shown.

FIGS. 11a-o show sustained elevation of intracellular zinc availability following egg activation leads to reestablishment of metaphase arrest. Eggs were activated with strontium chloride (SrCl2) then treated with zinc pyrithione (ZnPT) 1.5 hours later (a). At 6 h postactivation, control eggs form pronuclei (b, arrowheads) whereas the majority of eggs treated with ZnPT do not (c). When visualized by fluorescence, control eggs display decondensed DNA organized within a defined nucleus (d). F-actin is homogeneous around the egg's cortex (e) and α-tubulin remains organized as a spindle midbody remnant (f), which is visible between the egg and the second polar body (g, merged image). In contrast, ZnPT-treated eggs display condensed chromosomes (h) adjacent to an area of concentrated, cortical F-actin (i). α-tubulin is organized in a metaphase-like configuration (j) around the chromosomes (k, merged image). This layout mirrors the subcellular arrangement in unfertilized eggs (l-o), which also display condensed chromosomes (l) overlaid with an actin cap (m), surrounded by a metaphase spindle (n). Scale bar=80 µm (b, c) or 25 µm (d-o).

FIGS. 12a-e show perturbation of intracellular zinc availability causes activation of the egg. Following 8 hours of culture, control eggs maintain a metaphase II spindle (a, sp) with individual chromosomes aligned at the metaphase plate (b). In contrast, eggs exposed to 10 µM TPEN for the same period artificially activate as indicated by the formation of an intact pronucleus (c, pn) with decondensed chromatin surrounding a nucleolus (d). The number of eggs displaying a pronucleus is significantly higher in the TPEN-treated group (e).

FIGS. 13a-d show the chemical structure of an exemplary Zn-responsive probe of the present invention (A, A zinc-chelating ligand containing five potential zinc binding groups; B, BODIPY fluorophore; C, ethanol ether based linker chain; D, amine group that enables attachment of this fluorophore to carboxylate-modified surfaces via amide-coupling chemistries).

FIG. 22 shows ZincBY-1 is capable of labeling zinc-rich punctae in the mammalian egg at 50 nM concentration. Image is a 3D reconstruction of a z-stack of an MII mouse egg that has incubated in 50 nM ZincBY-1 to label zinc (green) and 0.1 mg/mL Hoechst to label DNA (blue). Scale bar=20 µm.

DETAILED DESCRIPTION

Figure 1:
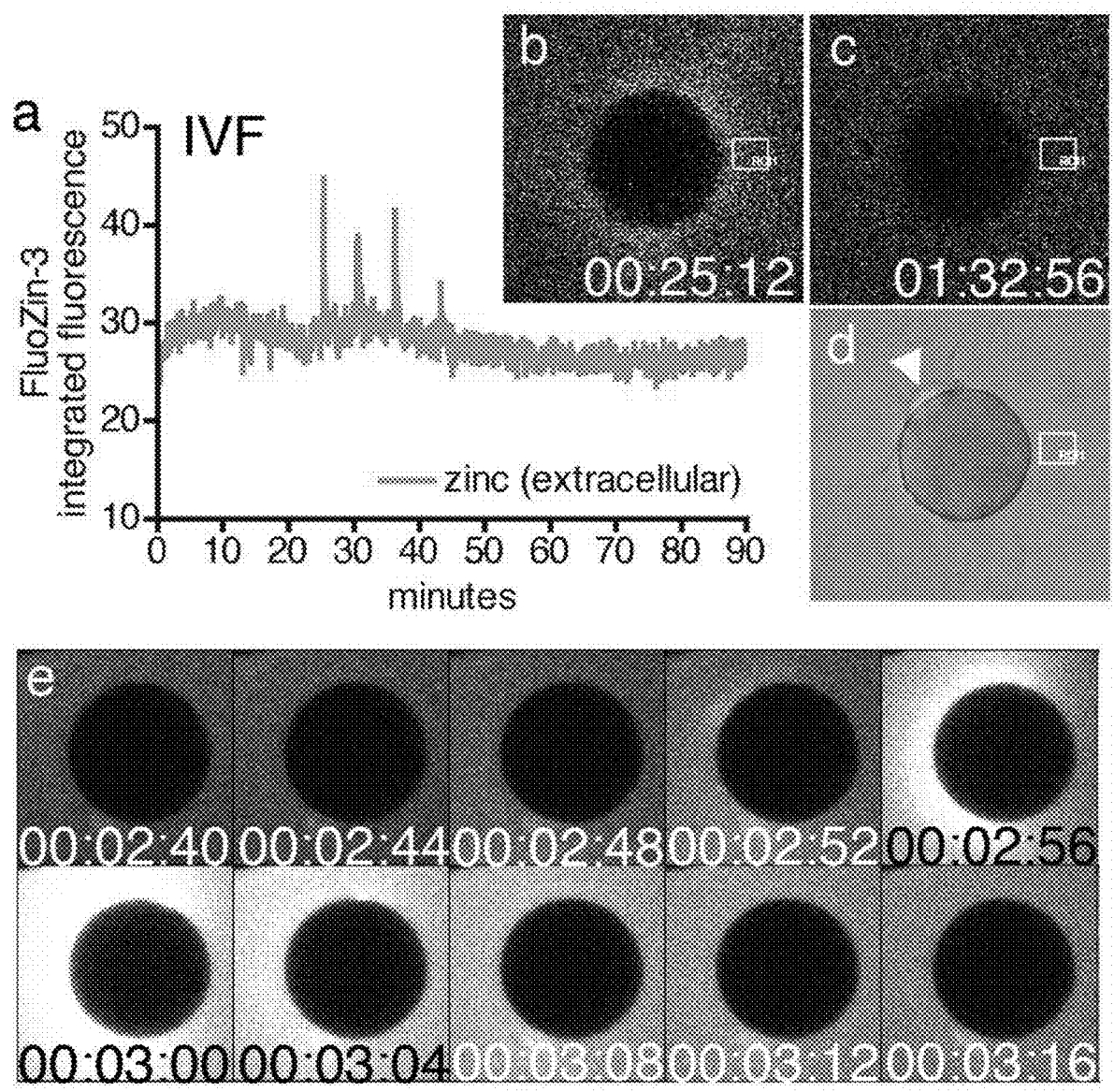
FIG. 1, Panels a-e show images depicting how changes in extracellular zinc concentration are readily monitored with FluoZin-3 during in vitro fertilization. Rapid, repetitive increases in fluorescence intensity were detected (a) by ROI analysis (denoted by white boxes in b-d). These spikes in fluorescent intensity involve the coordinated release of zinc from the cell in a phenomenon defined as a "zinc spark." Each zinc spark can be distinguished in the time-lapse series (b, 00:25:12) against background fluorescence (representative example in c, 01:32:56). Successful fertilization was confirmed by the extrusion of a second polar body (d). Zinc sparks were also noted during strontium chloride-induced parthenogenesis (e, 00:02:56).
Figure 2A:
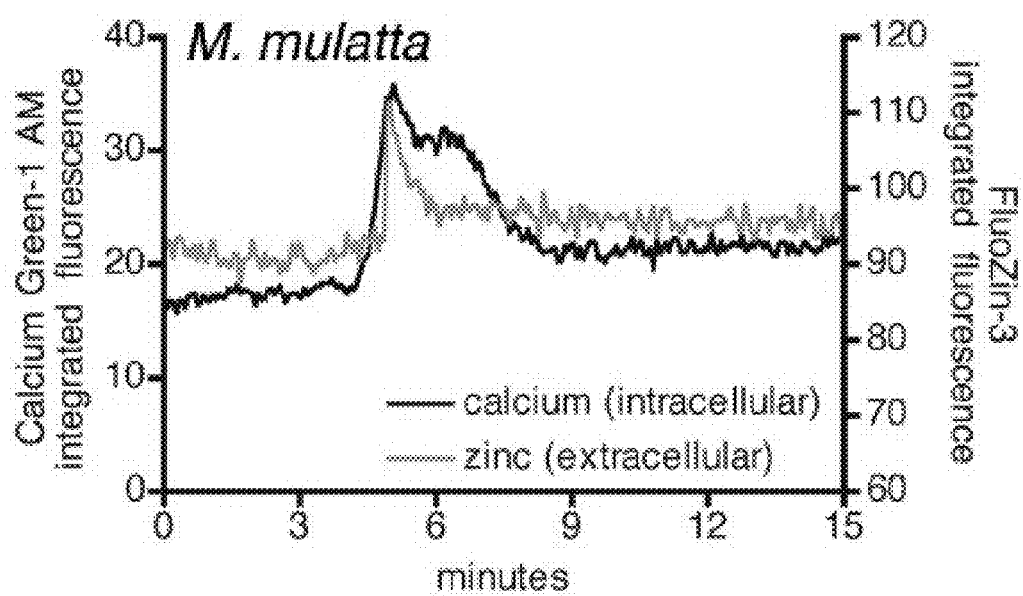
FIGS. 2*a-d* show zinc sparks observed in eggs from two different non-human primate species, *Macaca mulatta* (a, b) and *Macaca fascicularis* (c, d). In both cases, a single calcium transient was induced by ionomycin. Intracellular calcium was monitored with Calcium Green-1 AM, and extracellular zinc with FluoZin-3. The first panel begins at 00:04:35 in c and 00:06:37 in d. Each subsequent panel represents an image acquired 4 s following the previous panel. Time is expressed as hh:mm:ss, wherein 00:00:00 represents the start of image acquisition. Scale bar=40 µm in c and d.
Figure 2B:
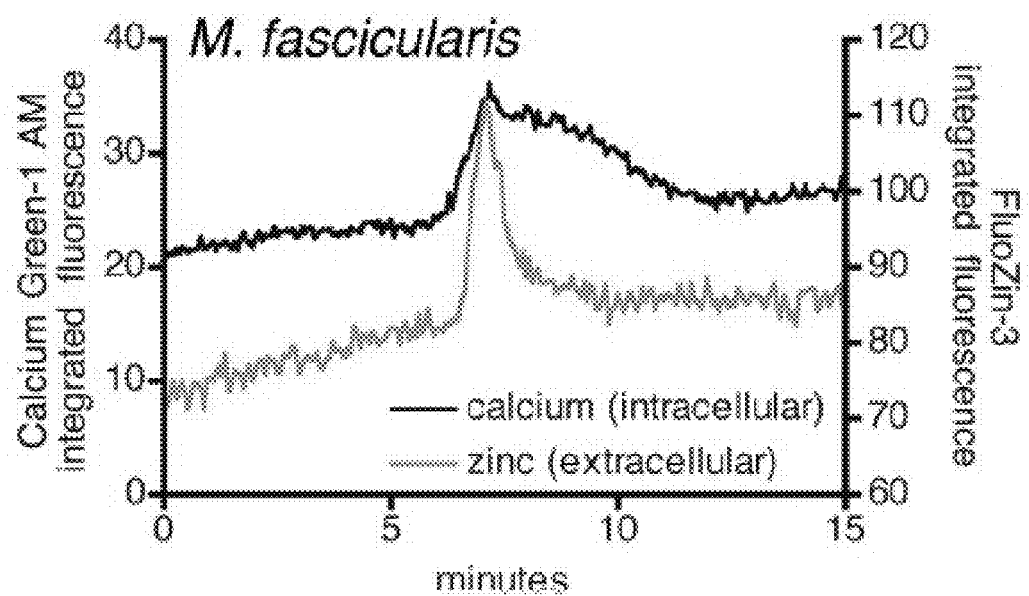
Figure 2C:
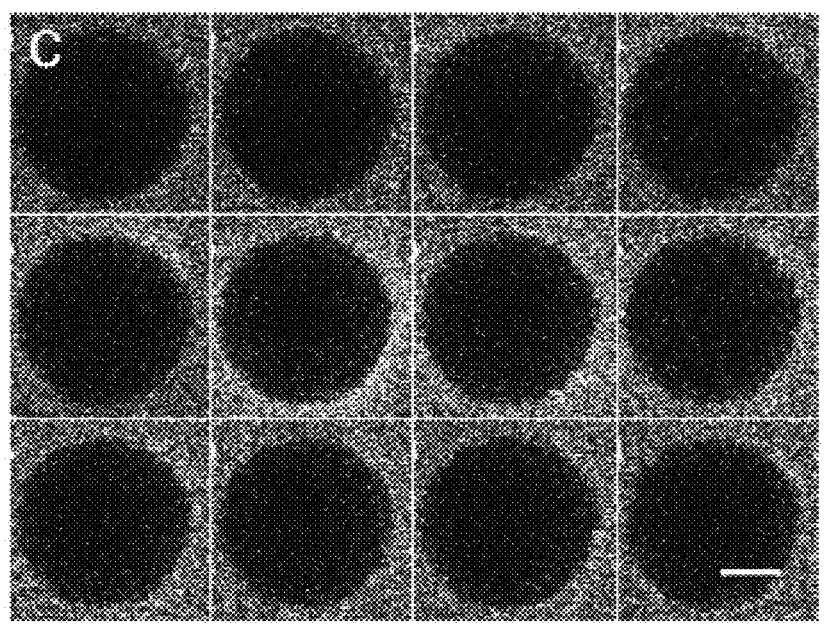
Figure 2D:
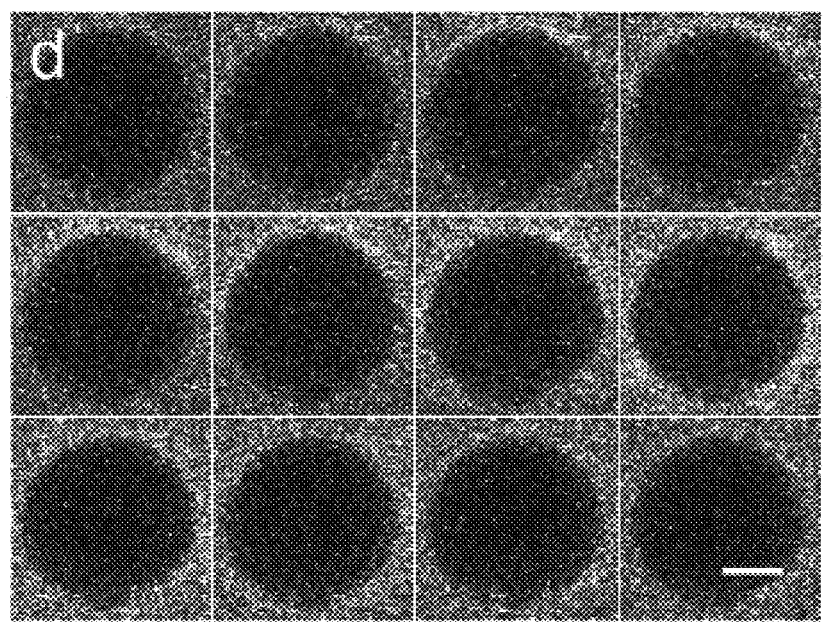

The invention relates generally to compositions and methods for the detection of zinc (Zn). In particular, compositions and methods are provided to detect changes in extracellular and/or intracellular zinc concentration and correlate them to cellular phenomena. Experiments conducted during development of embodiments of the present invention demonstrated the in vivo detection of changes in cellular (e.g., extracellular, intracellular) zinc levels and correlation of those levels to cellular events. In some embodiments, detection of changes in cellular (e.g., extracellular, intracellular) zinc levels provides a marker for the occurrence of cellular events (e.g., fertilization). In some embodiments, the present invention provides reagents (e.g., probes) for the in vivo and/or in vitro measurement of Zn levels or changes thereof. In some embodiments, the present invention provides methods for detection, measurement, and/or identification of changes in cellular Zn levels. In some embodiments, the present invention provides compositions and methods for detecting changes in Zn levels (e.g., intracellular, extracellular, non-cellular) and correlating such changes to cellular phenomena (e.g., cell cycle: phase, pausing, resumption, defects, etc.).

In some embodiments, the present invention provides one or more chemical probes comprising, consisting of, or consisting essentially of: A) a metal binding group (e.g., Zn-binding group, general metal chelator, etc.); B) a signaling moiety (e.g., fluorophore) that will exhibit a change in detectable signal (e.g., fluorescence properties) in response to metal ion binding to the metal binding group; C) a linker group; an attachment group that will allow for attachment of the probe to surfaces (e.g., plate, bead, well, slide, biopolynerm cell surface, etc) via coupling chemistries (e.g., amide coupling, thiol/maleimide chemistry, click chemistry, etc.).

I. Zn-Responsive Probes

In some embodiments, the present invention provides probes and other reagents for use in detecting Zn concentrations, levels, presence, or changes thereof. In some embodiments the present invention provides Zn-responsive chemical probes. In some embodiments, the probes and reagents provided herein provide intracellular, extracellular, or non-cellular detection and/or quantification of Zn, and/or changes in the presence or concentration of Zn, either in vivo or in vitro. In some embodiments, the probes described herein are capable of (1) detecting the presence of one or more Zn ions and/or Zn-containing compositions (e.g., by binding to Zn), and (2) signaling the detection of Zn ions and/or Zn-containing compositions (e.g., optically). In some embodiments, probes comprise one or more of: a Zn-binding group (ZB), a signaling moiety (S) (e.g., fluorophore), one or more linkers (Lx), and an attachment group (A). In some embodiments, a Zn-responsive probe comprises a Zn-binding group attached to a signaling moiety, optionally through a linker. In some embodiments, a Zn-binding group and signaling moiety are directly attached. In some embodiments, a Zn binding group and/or signaling moiety are covalently connected to an attachment group (e.g., through a linker, directly, etc.). In some embodiments, a Zn-responsive probe comprises a general structure selected from the group comprising:

(1) A—L—S—ZB
(2) A—L—ZB—S
(3) A—S—ZB
(4) A—S—L—ZB
(5) A—ZB—L—S
(6) A—L1—S—L2—ZB
(7) A—L1—ZB—L2—S
(8) S—ZB

In some embodiments, a Zn-responsive probe comprises a Zn-binding group and a signaling moiety. In some embodiments, the Zn-binding group comprises a chemical functionality to bind one or more Zn ions present in its local environment. In some embodiments, upon binding a Zn ion by the Zn-binding group, a structural, conformational, chemical, physical, or other change in the Zn-responsive probe causes a detectable change in the signal from the signaling moiety (e.g., shift in emission maximum, shift in excitation maximum, change in intensity, etc.). In some embodiments, detection or quantification of the signal from the signaling moiety provides a qualitative and/or quantitative means for detecting and/or measuring the presence or amount of Zn present in the probe's local environment. In some embodiments, detection or quantification of changes in the signal from the signaling moiety provides a qualitative and/or quantitative means for detecting and/or measuring changes in the presence or amount of Zn present in the probe's local environment.

In some embodiments, a Zn-responsive probe comprises a Zn binding group, and attachment group, and a signaling moiety. In such embodiments, the Zn binding group and signaling moiety function to bind Zn and provide a signal indicative of the binding event, as described in the preceding paragraph. In some embodiments, the attachment group is a chemical moiety capable of covalently or non-covalently interacting with another chemical moiety known as the anchor moiety. In some embodiments, interaction of the attachment group with the anchor moiety results in stable attachment of the Zn-responsive probe to the anchor moiety. In some embodiments an object or surface (e.g., plate, well, bead, slide, etc.) displays one or more anchor moieties. In some embodiments, interaction of the attachment groups of one or more Zn-responsive probes with one or more anchor groups displayed on a surface results in one or more Zn-responsive probes being displayed on the surface or object.

In some embodiments, a Zn-responsive probe comprises one or more structural or functional features described in U.S. Pat. No. 7,105,680; herein incorporated by reference in its entirety.

A. Zn-Binding Groups

In some embodiments, a Zn-responsive probe comprises a metal-binding group. In some embodiments, a metal binding group comprises a Zn-binding group. In some embodiments, a Zn-responsive probe comprises more than one Zn-binding groups (e.g., 2, 3, 4, 5, 6, 7, 8, 9, 10, etc.). In some embodiments, a Zn-binding group is a chemical moiety capable of stably interacting with one or more Zn ions. In some embodiments, a Zn-binding group is capable of interacting with one or more Zn ions, while covalently attached to the other functional elements of the Zn-responsive probe. In some embodiments, a Zn-binding group interacts with a Zn ion through covalent and/or non-covalent binding. In some embodiments, a Zn-binding group coordinates and/or partially coordinates a Zn ion. In some embodiments, a Zn-binding group is capable of coordinating a single Zn ion. In some embodiments, a Zn-binding group is capable of coordinating more than one Zn ions at a time (e.g., 2, 3, 4, 5, 6, 7, 8, 9, 10 . . . 20 . . . 50 . . . 100 . . . 1000, etc.). In some embodiments, coordination of a Zn ion results in a chemical, magnetic, electric, physical, and/or structural change in the Zn-binding group, the signaling moiety, the connection between the Zn-binding group and the signaling moiety, and/or the Zn-responsive probe. In some embodiments, the type, degree, and/or magnitude of the change are dependent or responsive to the number of Zn ions coordinated (e.g., more coordinated Zn ions results in greater change). In some embodiments the denticity and/or identity of Zn-binding groups is adjusted to tune metal binding affinity and selectivity.

In some embodiments, the present invention is not limited to any particular type or class of Zn-binding groups. In some embodiments, a Zn-binding group comprises a functional group capable of transiently or stably binding, coordinating, and/or chelating one or more Zn ions (e.g., free or in another complex). In some embodiments, a Zn-binding group is Zn specific. In some embodiments, a Zn-binding group preferentially binds Zn over other metal ions. In some embodiments, a Zn-binding group is a general metal-binding moiety. Chemical moieties that find use as Zn-binding groups, or within Zn-binding groups, of the present invention include, but are not limited to, e.g., diethyldithiocarbamate (DEDTC) and ethylenediaminetetra-acetic acid (EDTA), 1,10-phenanthroline, pyridyl-containing compounds, amine-containing compounds (e.g., tertiary amines), histidine containing compounds, sulfonamide-containing compounds, etc. In some embodiments, a Zn-binding group has at least one functional group selected from polyalkylene oxide, hydroxylated group, or a group having at least one amine, ammonium salt, carboxylate, sulfanyl, sulfinyl, sulfonyl, phosphate, phosphonate, phosphate, tertiary amine, pyridyl group; or combinations thereof. In some embodiments, Zn-binding groups comprise one or more sites for attachment to other functional groups within the Zn-responsive probe (e.g., attachment group, signaling moiety, linker, another Zn-binding group, etc.).

B. Signaling Moiety

In some embodiments, a signaling moiety is a detectable chemical moiety. In some embodiments, a signaling moiety is an optically detectable chemical moiety (e.g., fluorophore, chromophore, etc.). In some embodiments, a signaling moiety comprises a fluorescent dye or fluorophore. In some embodiments, a signaling moiety finds utility as a fluorophore for detection using one or more of optical spectroscopy, fluorescence spectroscopy, confocal spectroscopy, confocal fluorescence spectroscopy, two-photon excitation (TPE) fluorescence microscopy, etc.

In some embodiments, a signaling moiety is configured within a Zn-responsive probe such that coordination of one or more zinc ions by the Zn-binding group results in a detectable change in the signal from the signaling moiety. In some embodiments, a detectable change in signal comprises a change (e.g., increase or decrease) in signal (e.g., fluorescence) intensity. In some embodiments a detectable change (e.g., increase or decrease) in signal (e.g., fluorescence) intensity is readily detectable by a skilled artisan using the compositions and methods of the present invention (e.g., 1.1-fold . . . 1.2-fold . . . 1.5-fold . . . 2-fold . . . 5-fold . . . 10-fold . . . 20-fold . . . 50-fold . . . 100-fold . . . 200-fold . . . 500-fold . . . 1000-fold, etc.). In some embodiments, a detectable change in signal comprises a change (e.g., increase or decrease) in the excitation maximum. In some embodiments, a detectable change in signal comprises a change in the excitation spectrum. In some embodiments, a detectable change in signal comprises a change (e.g., increase or decrease) in the emission maximum. In some embodiments, a detectable change in signal comprises a change in the emission spectrum.

The present invention is not limited to any particular signaling moiety. In some embodiments, the signaling moiety is a fluorophore. The present invention is not limited to any particular fluorophore. Fluorophores and/or fluorescent labels that find use as or within signaling moieties of the present invention include, but are not limited to, e.g., fluorescein and rhodamine dyes, such as fluorescein isothiocyanate (FITC), 6-carboxyfluorescein (commonly known by the abbreviations FAM and F), 6-carboxy-2',4',7',4,7-hexachlorofluorescein (HEX), 6-carboxy-4',5'-dichloro-2',7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G ($R6G^5$ or $G^5$), 6-carboxyrhodamine-6G ($R6G^6$ or $G^6$), and rhodamine 110; cyanine dyes, e.g., Cy3, Cy5 and Cy7 dyes; alexa dyes, e.g., alexa fluor 555, alexa fluor 594; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc; BODIPY dyes and quinoline dyes; and derivities thereof. Suitable fluorescent labels include any of the variety of fluorescent labels disclosed in United States Patent Application Publication No. 20010009762, the disclosure of which is incorporated herein by reference. In some embodiments, signaling moieties comprise one or more sites for attachment to other functional groups within the Zn-responsive probe (e.g., attachment group, another signaling moiety, linker, Zn-binding group, etc.).

C. Linker

In some embodiments, present invention provides one or more linkers, linking moieties, linking groups, or linker regions. In some embodiments, a linker connects two or more functional groups of a Zn-responsive probe (e.g., signaling moiety, Zn-binding group, attachment group, etc.). In some embodiments, a linker comprises 1-1000 atoms (e.g., 1-10, 1-100, etc.). In some embodiments, a linker connects a signaling moiety to a Zn-binding group. In some embodiments, a linker connects a signaling moiety to an attachment group. In some embodiments, a linker connects an attachment group to a Zn-binding group. In some embodiments, one functional groups of a Zn-responsive probe (e.g., signaling moiety, Zn-binding group, attachment group, etc.) is connected to more than one other functional groups of a Zn-responsive probe (e.g., signaling moiety, Zn-binding group, attachment group, etc.) by multiple linkers. In some embodiments, a linker is branched for connection of three or more functional groups of a Zn-responsive probe (e.g., signaling moiety, Zn-binding group, attachment group, etc.).

The present invention is not limited to any particular linker group. Indeed, a variety of linker groups are contemplated, suitable linkers could comprise, but are not limited to, alkyl groups, ether, polyether, alkyl amide linker, a peptide linker, a modified peptide linker, a Poly(ethylene glycol) (PEG) linker, a streptavidin-biotin or avidin-biotin linker, polyaminoacids (e.g. polylysine), functionalized PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker, phospholipid derivatives, alkenyl chains, alkynyl chains, disulfide, or a combination thereof.

In some embodiments the linker comprises a single chain connecting one functional groups of a Zn-responsive probe (e.g., signaling moiety, Zn-binding group, attachment group, etc.) to another functional group of a Zn-responsive probe (e.g., signaling moiety, Zn-binding group, attachment group, etc.). In some embodiments, there are multiple linkers connecting multiple Zn-binding groups to a single signaling moiety. In some embodiments, a linker may connect multiple Zn-binding groups to each other. In some embodiments, a linker may connect multiple signaling moieties to each other. In some embodiments, a linker may be branched. In some embodiments, the linker may be flexible, or rigid.

In some embodiments, the linker of the present invention is cleavable or selectively cleavable. In some embodiments, the linker is cleavable under at least one set of conditions, while not being substantially cleaved (e.g. approximately 50%, 60%, 70%, 80%, 90%, 95%, 99%, or greater remains uncleaved) under another set (or other sets) of conditions. In some embodiments, the linker is susceptible to cleavage under specific conditions relating to pH, temperature, oxidation, reduction, UV exposure, exposure to radical oxygen species, chemical exposure, light exposure (e.g. photocleavable), etc. In some embodiments, the linker region is photocleavable. That is, upon exposure to a certain wavelength of light, the linker region is cleaved, allowing release of the connected functional groups (e.g., Zn-binding group, etc.). This embodiment has particular use in developmental biology fields (cell maturation, neuronal development, etc.), where the ability to follow the fates of particular cells is desirable. In some embodiments, a preferred class of photocleavable linkers are the O-nitrobenzylic compounds, which can be synthetically incorporated via an ether, thioether, ester (including phosphate esters), amine or similar linkage to a heteroatom (particularly oxygen, nitrogen or sulfur). Also of use are benzoin-based photocleavable linkers. A wide variety of suitable photocleavable moieties is outlined in the Molecular Probes Catalog, supra. In some embodiments, the linker is susceptible to enzymatic cleavage (e.g. proteolysis). In some embodiments of the present invention, functional groups (e.g., signaling moiety and Zn-binding group) are linked, via a cleavable linker. The present invention is not limited to any particular linker group. In some embodiments, the cleavable linker region contains a peptide portion. In some embodiments, the peptide portion of the cleavable linker region is cleavable. In some embodiments, the peptide portion of the cleavable linker region is enzymatically cleavable. In some embodiments the cleavable linker contains a specific proteolytic site. In some embodiments, in addition to the peptide portion of the cleavable linker region, an additional linker portion is contemplated. Indeed, a variety of additional linker groups are contemplated, suitable linkers could comprise, but are not limited to, alkyl groups, ether, polyether, alkyl amide linker, a peptide linker, a modified peptide linker, a Poly (ethylene glycol) (PEG) linker, a streptavidin-biotin or avidin-biotin linker, polyaminoacids (e.g. polylysine), functionalised PEG, polysaccharides, glycosaminoglycans, dendritic polymers (WO93/06868 and by Tomalia et al. in Angew. Chem. Int. Ed. Engl. 29:138-175 (1990), herein incorporated by reference in their entireties), PEG-chelant polymers (WO94/08629, WO94/09056 and WO96/26754, herein incorporated by reference in their entireties), oligonucleotide linker, phospholipid derivatives, alkenyl chains, alkynyl chains, disulfide, or a combination thereof.

D. Attachment Group

In some embodiments, an attachment group is configured for covalent and/or non-covalent binding/interaction with a surface (e.g., well, plate, bead, slide, etc.). In some embodiments, an attachment group is configured for covalent and/or non-covalent binding/interaction with an anchor moiety. In some embodiments, an attachment group and anchor moiety comprise an attachment pair. In some embodiments, an attachment group and anchor moiety are chemically or physically complimentary to allow a stable interaction (e.g., covalent or non-covalent) between them. In some embodiments, an attachment group is part of a Zn-responsive probe. In some embodiments, an anchor moiety is a functional group attached to a surface or object (e.g., plate, bead, well, slide, etc.). In some embodiments, the interaction of the members of an attachment pair provides a mean for attaching a Zn-responsive probe to a surface or object (e.g., plate, bead, well, slide, etc.). In some embodiments, the attachment pair interaction is reversible. In some embodiments, the attachment pair interaction is irreversible. In some embodiments, the interaction of the attachment pair is stable enough to provide stable attachment of the Zn-responsive element to a surface or object (e.g., plate, bead, well, slide, etc.) for at least the duration of Zn detection (e.g., experiment, evaluation, assay, treatment, diagnosis, etc.). The present invention is not limited by the type or class of attachment group. In some embodiments, attachment groups comprise, e.g., one or more chemical groups including, but not limited to: aldehyde, hydroxysuccinimidyl, hydrazide, thiol, triflate, tresylate, azirdine, oxirane, orthopyridyl disulphide, vinylsulfone, iodoacetamide or a maleimide, a group suitable for Click chemistry, etc.

In some embodiments, an attachment pair (e.g., attachment group and anchor moiety) provide chemical means for attaching a Zn-responsive probe to a surface (e.g., plate, bead, well, slide, etc.). The present invention is not limited by the types of attachment pairs, and any suitable attachment pair that allows for attachment of a Zn-responsive probe to an anchor-decorated surface may find use with the present invention (e.g., carboxylate and amine; thiol and maleimide; biotin and streptavidin; azide and phosphine, etc.).

In some embodiments, an attachment pair (e.g., attachment group and anchor moiety) provide chemical means for attaching a Zn-responsive probe to a surface (e.g., plate, bead, well, slide, etc.). The present invention is not limited by the types of surfaces, and any suitable surface or object may find use with the present invention, for example: beads, nanobeads, microparticles, microscope slide, microfluidics chamber, the interior of a reaction tube, a well (e.g., of a 96-well plate, of a 384-well plate, etc.), microtiter plate, etc.

In some embodiments, attachment of one or more Zn-responsive probes to a surface allows a sample to be added to the Zn-responsive probes, assayed for the presence, amount, or a change in Zn concentration, and then the sample is removed from the surface without contaminating the sample. In some embodiments, non-invasive sample assaying is provided by stably anchored Zn-responsive probes. In some embodiments, attachment of one or more Zn-responsive probes to a bead allows the Zn-responsive probes to be added to a sample; the sample is assayed for the presence, amount, or a change in Zn concentration; and then the bead-bound Zn-responsive probes are removed from the sample without contamination. In some embodiments, attachment of one or more Zn-responsive probes to a surface allows a sample to be added to the Zn-responsive probes without contamination of the sample with the probes. In some embodiments, attachment of one or more Zn-responsive probes to a surface allows cells (e.g., oocytes) to be added to the Zn-responsive probes without entry of the probes into the cells (e.g., preventing cell toxicity or disruption of cellular functions).

II. Methods/Applications

In some embodiments, the present invention provides methods for detection, measurement, identification, and/or quantification of Zn ions and/or Zn-containing compounds or compositions. In some embodiments, the present invention provides methods for detection, measurement, identification, and/or quantification of Zn concentration. In some embodiments, the present invention provides methods for detection, measurement, identification, and/or quantification of changes in Zn concentration. In some embodiments, the present invention provides methods for correlating biological and/or cellular events, changes, processes, and/or phenomena to Zn concentration or changes thereof (e.g., extracellular Zn concentration, intracellular Zn concentration, etc.). In some embodiments, any suitable methods of detecting and/or quantifying the presence and/or concentration of Zn ions, or changes thereof, find use in the present invention. In some embodiments, Zn ions are detected and or quantified through the use of Zn-sensitive probes, e.g., those described herein.

In some embodiments, the present invention provides detection or quantification of changes in intracellular and/or extracellular Zn concentration and correlates those changes to changes in the cell cycle (e.g., stall, pause, arrest, resumption). In some embodiments, the compositions and methods herein provide correlation of Zn concentration (e.g., extracellular Zn concentration) to the cell cycle phase of an oocyte (e.g., maturing oocyte) and/or is progression through the maturation process. In some embodiments, methods provided herein detect and/or quantify Zn uptake or release from cells. In some embodiments, methods correlate Zn uptake or release from cells with cellular activity (e.g., cell cycle activities (e.g., moving from one phase to another, arrest of cell cycle, resumption of cell cycle)).

Experiments were conducted during development of the present invention to determine whether zinc regulation of meiotic progression extended to cell cycle regulation in the fertilized egg. The dynamics of zinc and calcium within the physiological context of fertilization were examined using a variety of chemical probes, which revealed that calcium oscillations induced a rapid loss of zinc through an event termed the zinc spark. Experiments conducted during development of the present invention demonstrated that zinc sparks (i.e., Zn release from cells (e.g., oocytes) are evolutionarily conserved in three mammalian species, and that these fluxes in intracellular zinc availability mediate cell cycle resumption. Experiments conducted during development of the present invention demonstrate a zinc-dependent mechanism for cell cycle regulation in the mammalian egg. Calcium oscillations initiate and are required for the programmed loss of cellular zinc via the zinc sparks and that in turn drives cell cycle resumption.

Experiments conducted during development of embodiments of the present invention demonstrate that intracellular Zn levels in maturing oocytes rise dramatically as the cell matures from prophase-I to metaphase-II. This rise in Zn levels corresponds to uptake in Zn ions from the extracellular environment. Cells that do not undergo this Zn acquisition do not progress to metaphase-II arrest, and are not candidates for fertilization. Cells that do not acquire the requisite intracellular Zn ion concentration proceed to telophase-I arrest and are of poor quality for fertilization (e.g., unlikely to be successfully fertilized). Detection of the uptake of Zn ions by oocytes maturing from prophase-I to metaphase-II provides a marker for healthy, normal maturation of oocytes. Detection of the uptake of Zn ions by oocytes maturing from prophase-I to metaphase-II provides a marker for oocytes that are good candidates for fertilization (e.g., via in vitro fertilization (IVF), via in vitro maturation (IVM), etc.). In some embodiments, the present invention provides compositions (e.g., Zn-responsive probes) and methods for the detection of uptake of Zn ions by cells (e.g., oocytes) from the extracellular environment. In some embodiments, the present invention provides compositions (e.g., Zn-responsive probes) and methods for correlating the uptake of Zn ions by cells (e.g., oocytes) from the extracellular environment with cellular phenomena (e.g., progress from prophase-I to metaphase-II).

Further experiments demonstrated that one or more rapid decreases in intracellular Zn concentration occur following fertilization of a metaphase-II oocyte. These decreases in intracellular Zn levels correspond to rapid releases of Zn (e.g., Zn sparks) from oocytes into the extracellular environment. Upon successful fertilization, oocytes exhibit one or more Zn sparks (e.g., 2-7, 3-5, 1-10, at least 3, at least 4, at least 5, etc.). Detection of the release of Zn ions from oocytes following fertilization (e.g., Zn sparks) provides a marker for healthy, normal maturation of oocytes from metaphase-II arrest to a two-cell embryo. Detection of the Zn ion release (e.g., Zn sparks) by oocytes provides a marker for oocytes that that have been successfully fertilized (e.g., by IVF). In some embodiments, the present invention provides compositions (e.g., Zn-responsive probes) and methods for the detection of the release of Zn ions from cells (e.g., oocytes) into the extracellular environment. In some embodiments, the present invention provides compositions (e.g., Zn-responsive probes) and methods for correlating the release of Zn ions from cells (e.g., oocytes) into the extracellular environment with cellular phenomena (e.g., fertilization).

In some embodiments, the present invention provides compositions and methods for the detection of Zn release and/or uptake from cells, and correlation thereof to cellular phenomena. In some embodiments, such detection and correlation find use as a marker of cellular phenomena and/or cellular progression. In some embodiments, provided are methods for the non-invasive selection of quality eggs (e.g., high quality, e.g., matured to metaphase-II) for human IVF. In some embodiments, provided are methods for non-invasive selection of high quality eggs (e.g., matured to metaphase-II) for domestic animal and/or companion animal IVF. In some embodiments, provided are methods for non-invasive selection of high quality eggs (e.g., from any species) for use in the derivation of stem cells. In some embodiments, provided herein are functional marker for progression of egg (e.g., human, non-human) in IVM (e.g., with the purpose of freezing only good quality eggs).

The compositions and methods of the present invention are not limited to applications regarding oocyte cell cycle (e.g. detection of: cell cycle phase, stalling, pausing resumption, etc.). In some embodiments, the compositions and methods herein find utility in any cell types (e.g., oocyte, sperm cell, islets, neurons, etc.), as well as in cell lysate or non-cellular conditions.

In some embodiments, zinc concentration and/or changes in zinc concentration are detected in pancreatic islet cells (e.g., to identify islet cells capable of reacting properly to glucose concentration, to identify islet cells capable of appropriately releasing insulin, etc.). In some embodiments, zinc concentration and/or changes in zinc concentration are detected in pancreatic islet cells to evaluate the quality of the cells for potential use in islet cell transplant therapy. In some embodiments, the present invention provides methods for monitoring islet cell activation.

In some embodiments, zinc concentration and/or changes in zinc concentration are detected in sperm cells to evaluate sperm quality (e.g., for fertility treatment and/or evaluation).

In some embodiments, zinc concentration and/or changes in zinc concentration are detected in neuronal cells (e.g., to detect proper Zn release, to detect diseases of the nervous system (e.g., Parkinson's, Alzheimer's, etc.). In some embodiments, the present invention provides methods for monitoring neuron development. In some embodiments, zinc concentration and/or changes in zinc concentration are detected in neural cells to evaluate cell quality (e.g., appropriate levels and timing of metal (e.g., Zn) release) for neural cell transplant therapies.

In some embodiments, the present invention is not limited to detection or cellular, intracellular, or extracellular zinc. In some embodiments, methods and compositions herein are suitable for detection of zinc in any sample (e.g., biological (e.g., blood, urine, saliva, etc.), environmental (e.g., soil, water, contaminant, waste, etc.), veterinary, clinical, etc.)

Experimental

EXAMPLE 1

Materials and Methods

Mouse egg collection. Eggs were collected from adult (6-8 weeks old) female mice of the CD-1 strain. Micewere super stimulated with an i.p. injection of 5 IU pregnant mare's serum gonadotropin (PMSG, EMD Biosciences, San Diego, Calif.), followed 46-48 h later by an i.p. injection of 5 IU human chorionic gonadotropin (hCG, Sigma-Aldrich, St. Louis, MO.). Mice were sacrificed by CO2 asphyxiation and cervical dislocation 13-14 h post-hCG administration. Clutches of cumulus-oocyte complexes were isolated from the oviducts. Cumulus cells were denuded using 30 µg/ml hyaluronidase and gentle aspiration through a narrow-bore pipette. Animals were treated in accord with the National Institutes of Health Guide for the Care and Use of Laboratory Animals. Food and water were given ad libitum. The Northwestern University Institutional Animal Care and Use Committee (IACUC) approved all protocols.

Time-lapse imaging of mouse eggs during in vitro fertilization. Sperm from the cauda epididymides of proven breeder CD-1 males were used for sperm in vitro fertilization (IVF). The sperm population was purified using Percoll gradient centrifugation (PGC) as described previously (Xu et al. (2006), *Biol Reprod* 75, 916-23.; herein incorporated by reference in its entirety)) and capacitated for up to 3 h in IVF medium composed of potassium simplex optimized medium (KSOM, Millipore, Billerica, Mass.) supplemented with 3 mg/ml bovine serum albumin (BSA, MP Biomedicals, Solon, Ohio) and 5.36 mM D-glucose (Sigma-Aldrich). Superovulated eggs were collected as described above. The zona pellucida (ZP) was removed by brief treatment in acidic Tyrode's solution (pH 2.5, Millipore). The ZP-free eggs were allowed to settle in a 50 µl drop of calcium- and magnesium free Dulbecco's PBS (DPBS, Invitrogen, Carlsbad, Calif.) on a glass-bottom dish (Bioptechs Inc., Butler, Pa.) coated with poly-L-lysine. After 10 min, IVF medium containing 20 µM FluoZin-3 (Invitrogen) was slowly added to a final volume of 1 ml, taking care not to disturb the eggs. The final DMSO concentration was 0.1% (v/v), as higher concentrations were cytotoxic to sperm. Capacitated sperm were added to the eggs to a final concentration of $1.0 \times 10^6$ sperm/ml and image acquisition began immediately upon addition of sperm. Images were acquired every 4 sec for a total duration of 3 hours. All images were acquired on a TCS SP5 confocal microscope (Leica Microsystems, Heidelberg, Germany) equipped with a stage top incubator (Tokai Hit, Shizuoka, Japan), 20× objective, and an Ar (488 nm) laser line.

Parthenogenetic activation and pyrithione treatment of mouse eggs. Strontium chloride (SrCl2) was prepared as a 1 M stock solution in calcium-free KSOM (Millipore) and stored as ready-to-use aliquots at −20° C. SrCl2 was diluted to a working concentration of 10 mM in calcium-free KSOM. Eggs were incubated in SrCl2 for 90 min. In some cases, eggs were then treated with zinc pyrithione (ZnPT, Sigma-Aldrich). Dose response experiments were performed to test cytotoxicity; a distinct cytotoxic effect was seen at concentrations above 20 µM. Therefore, ZnPT concentrations were reduced to 10 µM and treatment time was limited to 10 min at 37° C. in an atmosphere of 5% CO2. Both control and ZnPT-treated eggs were washed and transferred to fresh KSOM for extended culture.

Non-human primate oocyte collection, in vitro maturation, and parthenogenetic activation. Ovarian tissue was surgically dissected from *Macaca mulatta* (rhesus macaque, 3 years old) and *Macaca fascicularis* (crab-eating macaque, 3 years old) females at the Panther Tracks Learning Center (Immokalee, Fla.). The tissue was cut in half, placed in 15 ml of SAGE oocyte washing medium (Cooper Surgical, Trombull, Conn.), and shipped overnight at ambient temperature. The tissue was processed within 18 hours of surgery. Large follicles were opened by grazing with an insulin-gauge needle. Oocytes of diameter greater than 100 µm (including the zona pellucida) were collected for in vitro maturation (IVM), whether they were enclosed by cumulus cells or denuded. They were placed in an IVM medium composed of SAGE oocyte maturation medium (Cooper Surgical) supplemented with 75 mIU/µl follicle stimulating hormone (FSH, a gift from Organon, Roseland, N.J.), 75 mIU/µl luteinizing hormone (LH, a gift from Ares Serono, Randolph, Mass.), 1.5 IU/µl hCG (Sigma-Aldrich), and 5 ng/ml epidermal growth factor (EGF, BD Biosciences, San Jose, Calif.). Oocytes were observed up to 48 hours post-maturation and used immediately for imaging upon complete extrusion of a polar body.

Time-lapse imaging of parthenogenetically activated eggs. Eggs were first incubated in 10 µM Calcium Green-1 AM (Invitrogen) and 0.04% (w/v) Pluronic F-127 (Invitrogen) for either 30 min (mouse) or 60 min (non-human primate) at 37° C. Mouse eggs were washed in calcium-free KSOM (Millipore) and transferred to a 50 µl drop containing 10 mM SrCl2 (Sigma-Aldrich) and 50 µM FluoZin-3 (Invitrogen) on a glass-bottom dish (Bioptechs Inc.). Non-human primate eggs were transferred to one end of a long and shallow drop (20 µl) of calcium-free KSOM (Millipore) containing 50 µM FluoZin-3 (Invitrogen) on a glass-bottom dish (Bioptechs Inc.), covered with oil for embryo culture (Irvine Scientific, Santa Ana, Calif.). Ionomycin was perfused in at the opposite end to a final concentration of 20 µM. In both cases, image acquisition began immediately and occurred every 4 s for a total of 1-3 hours (mouse) or 15 min (non-human primate), unless noted otherwise. All images were acquired on a TCS SP5 confocal microscope (Leica Microsystems) equipped with a stage top incubator (Tokai Hit), 20× objective, and an Ar (488 nm) laser line.

Imaging of total and labile zinc in the mouse egg. Fertilized eggs were collected at two and six hours post-fertilization were prepared whole-mount for synchrotron-based x-ray fluorescence microscopy (XFM). Cells were transferred with a minimal amount of media to an intact 5 mm×5 mm silicon nitride window (Silson, Blisworth, U.K.) on a heated stage warmed to 37° C. When most of the media had evaporated without drying out the sample, 1 µl of ammonium acetate solution (100 mM, 4° C.) was administered to each sample under a dissection microscope. This facilitated a quick wash and dehydration process, leaving the morphology of the sample intact without causing membrane rupture. XFM was performed at Beamline 2-ID-E at the Advanced Photon Source (Argonne National Laboratory, Argonne, Ill.). 10 keV x-rays were monochromatized with a single bounce Si(111) monochromator, and focused to a spot size of 0.5×0.6 µm using Fresnel zone plate optics (X-radia, Concord, Calif.). Raster scans were done in steps of 1 µm. Fluorescence spectra were collected with a 1 sec dwell time using a silicon drift detector (Vortex-EM, SII NanoTechnology, CA). Quantification and image processing was performed with MAPS software. The fluorescence signal was converted to a two-dimensional concentration in µg/cm2 by fitting the spectra against the thin-film standards NB S-1832 and NBS-1833 (National Bureau of Standards). It was assumed that no elemental content was lost during sample preparation. The data was compared to the total zinc content in unfertilized eggs and two-cell embryos. The data for the two-cell embryo was already published in a previous report14. The distribution of labile zinc was interrogated in live, unfertilized mouse eggs using two independent zinc fluorophores, zinquin ethyl ester (Sigma-Aldrich) and FluoZin-3 AM (Invitrogen). Eggs were incubated in either 20 µM zinquin ethyl ester in combination with 1 µM Syto 64 (Invitrogen) or 10 µM FluoZin-3 AM in combination with 10 µg/ml Hoechst 33342 (Invitrogen) for 60 min in KSOM (Millipore). They were imaged in 20 µl drops of KSOM covered with oil for embryo culture (Irvine Scientific) on glass-bottom dishes (Bioptechs Inc.). Images were acquired as Zstacks on a TCS SP5 confocal microscope (Leica Microsystems) equipped with a stage top incubator (Tokai Hit), 63× oil-immersion objective, and HeNe (543 nm), Ar (488 nm), and near-UV (405 nm) laser lines.

TPEN treatment and spindle imaging of mouse eggs. Superovulated eggs were collected and transferred to KSOM medium (Millipore) with or without 10 µM TPEN and cultured up to 8 hrs at 37° C. in an atmosphere of 5% CO2 in air. Previous work showed that treatment of maturing oocytes with 10 µM TPEN could selectively limit the intracellular acquisition of zinc (relative to iron and copper) but without significant toxicity14. Eggs were fixed and permeabilized for 30 min at 37° C. in a solution containing 2% formaldehyde, 2% Triton X-100, 100 mM PIPES, 5 mM MgCl2, and 2.4 mM EGTA. Eggs were then washed and blocked for 1-3 hrs in 1× PBS containing 0.1 M glycine, 3 mg/mL BSA, 0.01% Tween-20, and 0.01% sodium azide followed by incubation with anti- <-tubulin (1:100, Sigma) in blocking buffer for 1 hr at 37° C. Eggs were washed again in blocking buffer, incubated in Alexa Fluor 488-conjugated goat anti-mouse IgG (Invitrogen) and rhodamine-phalloidin conjugate (Invitrogen) at 37° C. for 1 hr, washed three additional times, and mounted on microscopy slides with coverslips in Vectashield with DAPI. Images were acquired as Z-stacks on a TCS SP5 confocal microscope (Leica Microsystems) equipped with a stage top incubator (Tokai Hit), 63× oil-immersion objective, and HeNe (543 nm), Ar (488 nm), and near-UV (405 nm) laser lines.

EXAMPLE 2 Release of Zinc at Egg Activation is a Conserved Event in Mammalian Species In experiments conducted during development of embodiments of the present invention extracellular zinc events were monitored during fertilization of mouse eggs using a membrane impermeant derivative of the zinc fluorophore FluoZin-3 (Qian & Kennedy. (2002) *J Am Chem Soc* 124, 776-8.; herein incorporated by reference in its entirety). Strikingly, fertilization triggered the repetitive release of zinc into the extracellular milieu (SEE FIGS. 1A and 1B). These events were termed zinc sparks for their brevity and intensity. Successful fertilization was confirmed by extrusion of the second polar body (SEE FIGS. 1C and 1D, PB2). These events were recapitulated during parthenogenesis of mouse eggs (SEE FIG. 1E). Zinc sparks are an evolutionarily conserved phenomenon, as they were also observed during parthenogenetic activation of two different non-human primate species, *Macaca mulatta* (rhesus macaque) and *Macaca fascicularis* (crab-eating macaque) (SEE FIG.

2). Additional characterization of the zinc sparks was completed using parthenogenetically activated mouse eggs.

The dynamics of the zinc sparks were variable from egg to egg. Zinc sparks occurred during the first 90 min of activation, and individual eggs exhibited between one and five zinc sparks, which were counted in a plot of fluorescence intensity over time (SEE FIG. 1A). Eighty-one percent of all eggs examined exhibited two or three exocytosis events, while eleven percent exhibited one event and eight percent exhibited four or five events. No more than five zinc sparks were observed in any of the samples. The interval between each exocytic event was 9.5±0.8 min (mean±SEM). The range of intervals was between 3.46 and 26.00 min.

Zinc sparks could be induced by fertilization or by parthenogenesis using two different reagents: strontium chloride in rodents and ionomycin in two non-human primate species. While strontium chloride induces multiple calcium transients whereas ionomycin only induces a single calcium transient (Kline & Kline. (1992) *Dev Biol* 149, 80-9.; Markoulaki et al. (2003) *Dev Biol* 258, 464-74.; herein incorporated by reference in their entireties). Accordingly, multiple zinc sparks were observed in rodents whereas only a single zinc spark was seen in the non-human primate species. This result indicates calcium dependence of the zinc sparks.

EXAMPLE 3

Initiation of the Zinc Sparks is Dependent on Intracellular Calcium Transients

Experiments were conducted during development of embodiments of the present invention to determine the role of zinc sparks within the temporal context of the calcium oscillations. Intracellular calcium oscillations were simultaneously monitored alongside zinc sparks using the calcium fluorophore Calcium Green-1 AM (ex. 506, em. 531), which has similar excitation and emission spectra to FluoZin-3 (SEE FIG. 3A). Each zinc spark was closely associated with an intracellular calcium transient (SEE FIG. 3B); upon closer inspection, it was found that each zinc spark was immediately preceded by an elevation in intracellular calcium (SEE FIG. 3C). Parallel experiments employing a membrane permeable zinc fluorophore, FluoZin-3 AM, did not reveal clear intracellular zinc transients (SEE FIG. 4A), ruling out the possibility that large oscillations in intracellular free zinc contributes to the intracellular transients detected by Calcium Green-1 AM. It was confirmed that this was representative of successfully activated eggs by simultaneously monitoring second polar body (PB2) extrusion by brightfield imaging (SEE FIG. 4A). Further control experiments employing one fluorophore at a time reveal that the zinc sparks are not dependent upon or effected by the presence of the calcium probe; for example, detection of zinc sparks using FluoZin-3 in the absence of Calcium Green-1 AM (SEE FIG. 1A (fertilization) and FIG. 1E (parthenogenesis)).

The observation that calcium transients immediately preceded each zinc release event indicates that the zinc sparks are directly dependent on intracellular calcium fluxes. Additional experiments were consistent with this determination. First, Zinc sparks did not occur in the absence of an activating agent and hence, a lack of calcium oscillations (SEE FIG. 4B). Second, zinc sparks were absent in eggs treated with the membrane permeable acetoxymethyl ester (AM) derivative of 1,2-bis(o-aminophenoxy)ethane-N,N,N', N'-tetraacetic acid (BAPTA). This reagent is commonly used to suppress calcium oscillations in eggs (Kline & Kline. (1992) *Dev Biol* 149, 80-9.; Tahara et al. (1996) *Am J Physiol* 270, C1354-61.; herein incorporated by reference in their entireties) and as such, both calcium transients and zinc sparks were absent in BAPTA AM-treated eggs even after extended culture in strontium chloride (SEE FIG. 4C). Furthermore, these eggs did not extrude a second polar body or form a pronucleus (SEE FI. 4D and 4E). Taken together, these data indicate that the zinc sparks are preceded by and depend upon the calcium oscillations that begin early in the egg activation process.

EXAMPLE 4

Localization of Zinc is Cortically Polarized in Mature Eggs

Figure 3A:
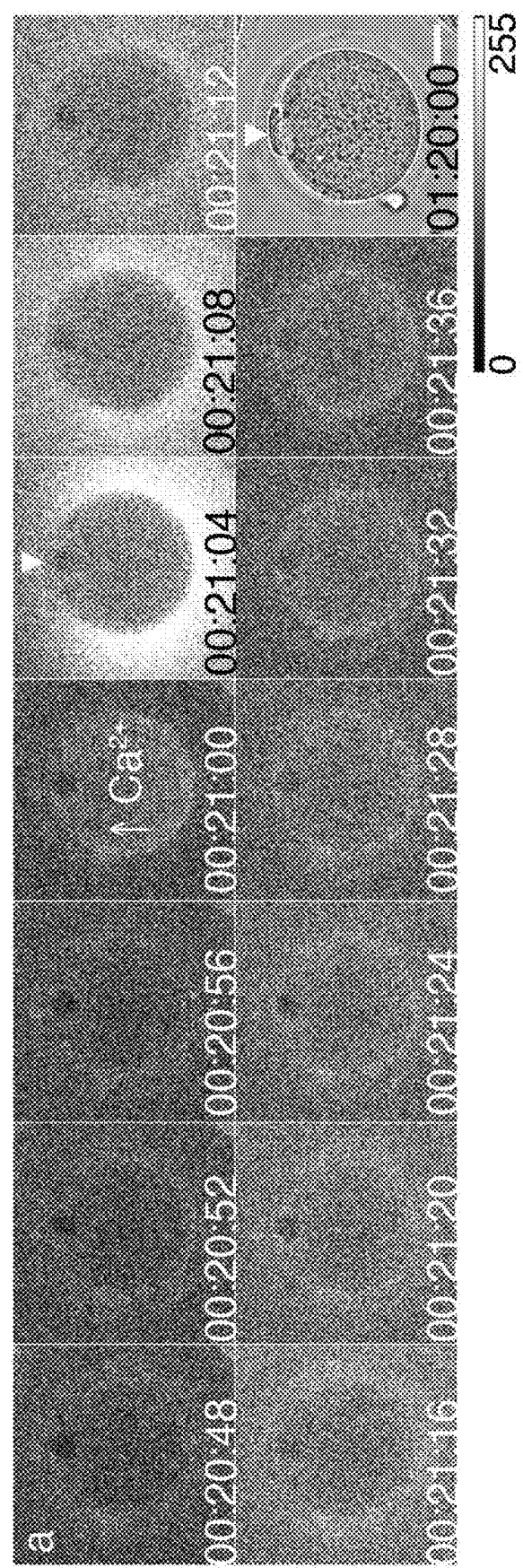
Figure 5A:
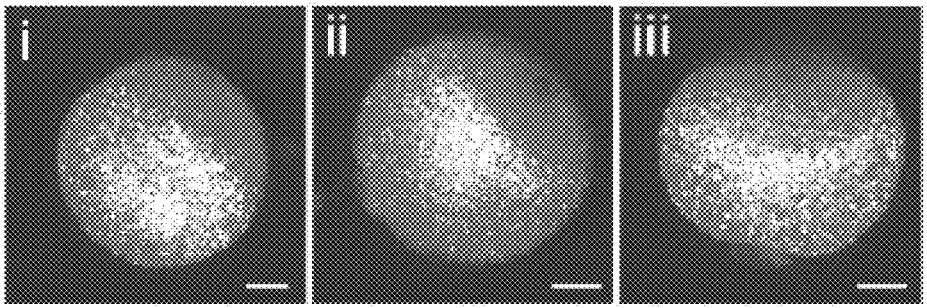
FIGS. 5a-h show images depicting cortically polarized zinc ions in the mouse egg. Total zinc, as detected by synchrotron-based x-ray fluorescence (a, b), is uniquely polarized in the unfertilized egg (a; i-iii represent replicates). This distribution is absent in the other essential transition elements, such as iron (b; i-iii represent replicates). The range of each group of images is given units of µg/cm2. Labile (chelator-accessible) zinc, as detected by confocal microscopy (c-h), also has a hemispherical distribution in the live egg, as detected by two chemically distinct zinc fluorophores: zinquin ethyl ester (c-e) and FluoZin-3 AM (f-h). Co-staining with a DNA marker (Syto 64 in d, Hoechst 33342 in g) revealed that zinc was concentrated at the vegetal pole away from the meiotic spindle.
Figure 5B:
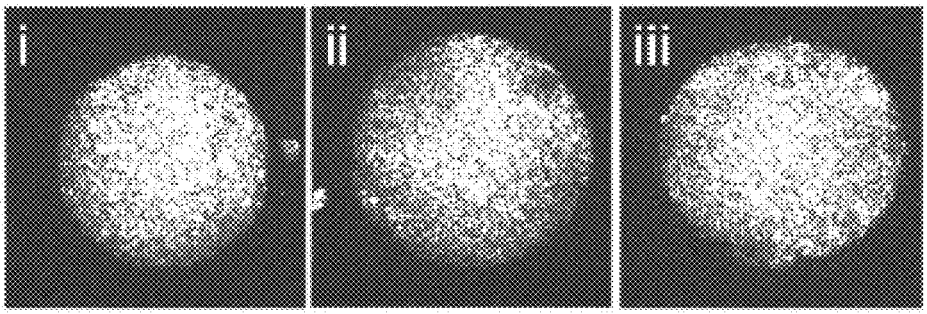
Figure 6:
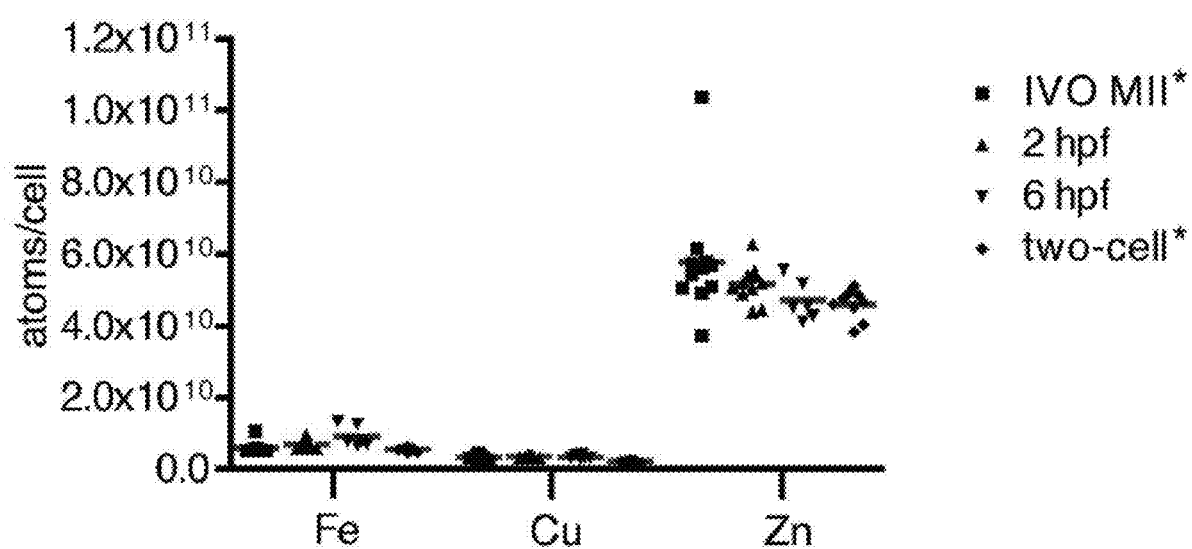
FIG. 6 shows total zinc content of the egg gradually decreases upon fertilization. Eggs and embryos were analyzed by XFM for their transition metal content. The mean zinc quota was highest in the in vivo ovulated (IVO) MII egg and trended towards a decrease following fertilization (see 2 and 6 hpf), reaching its lowest mean abundance in the two-cell embryo. The iron and copper quotas were an order of magnitude less than zinc at all time points examined.

Zinc sparks were excluded from the region corresponding to the location of the meiotic spindle, as confirmed by the extrusion of the second polar body at that site (SEE FIG. 3A, arrowheads). To investigate possible cellular sources of the zinc release, the distribution of zinc was determined in unfertilized eggs by synchrotron-based x-ray fluorescence microscopy (XFM). This technique provides the localization and abundance of the total zinc content of a sample, including both the loosely bound (labile or chelatable) and tightly bound cellular pools, and was previously used to quantify zinc and other transition metals in maturing oocytes (Kim et al. (2010) *Nat Chem Biol* 6, 674-81.; herein incorporated by reference in its entirety). The XFM images revealed distinct regions of high zinc concentration that formed a polarized and hemispherical pattern (SEE FIG. 5A; i-iii represent three independent samples). Other essential transition metals such as iron exhibit a homogeneous distribution across the entire cell (SEE FIG. 3B; i-iii represent three independent samples). Quantitative analysis revealed that zinc was an order of magnitude more abundant than either iron or copper at all points between the mature, in vivo ovulated (IVO) MII stage egg and the two-cell embryo (24 hours post-fertilization, or hpf). There is a downward trend with a mean loss of about six billion ions of zinc upon fertilization, and this trend continued at 6 hpf and 24 hpf (SEE FIG. 6). ANOVA analysis noted a significant difference in the mean zinc content across the four timepoints. Fluorescence imaging of intracellular zinc confirmed that the amount of chelatable zinc also decreased in activated eggs following the zinc sparks (SEE FIG. 7).

Figure 5C:
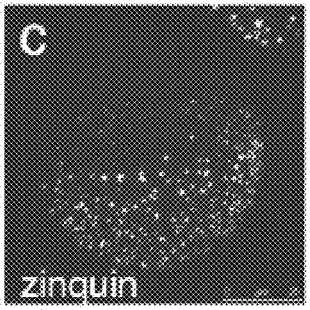
Figure 5D:
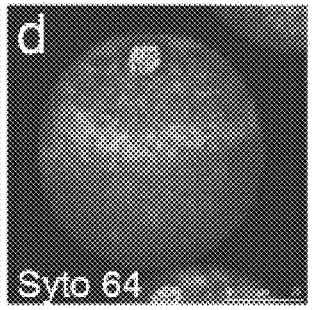
Figure 5E:
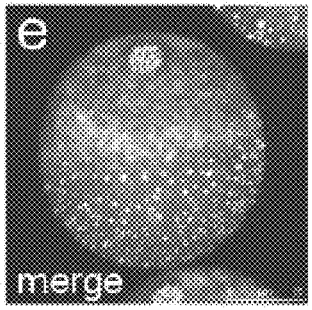
Figure 5F:
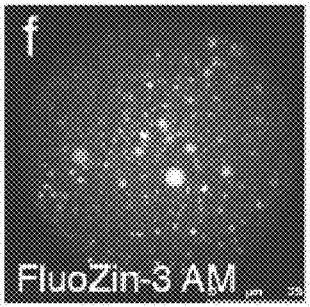
Figure 5G:
Figure 5H:
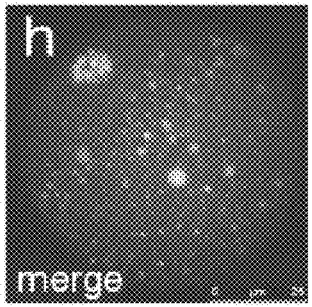
Figure 8:
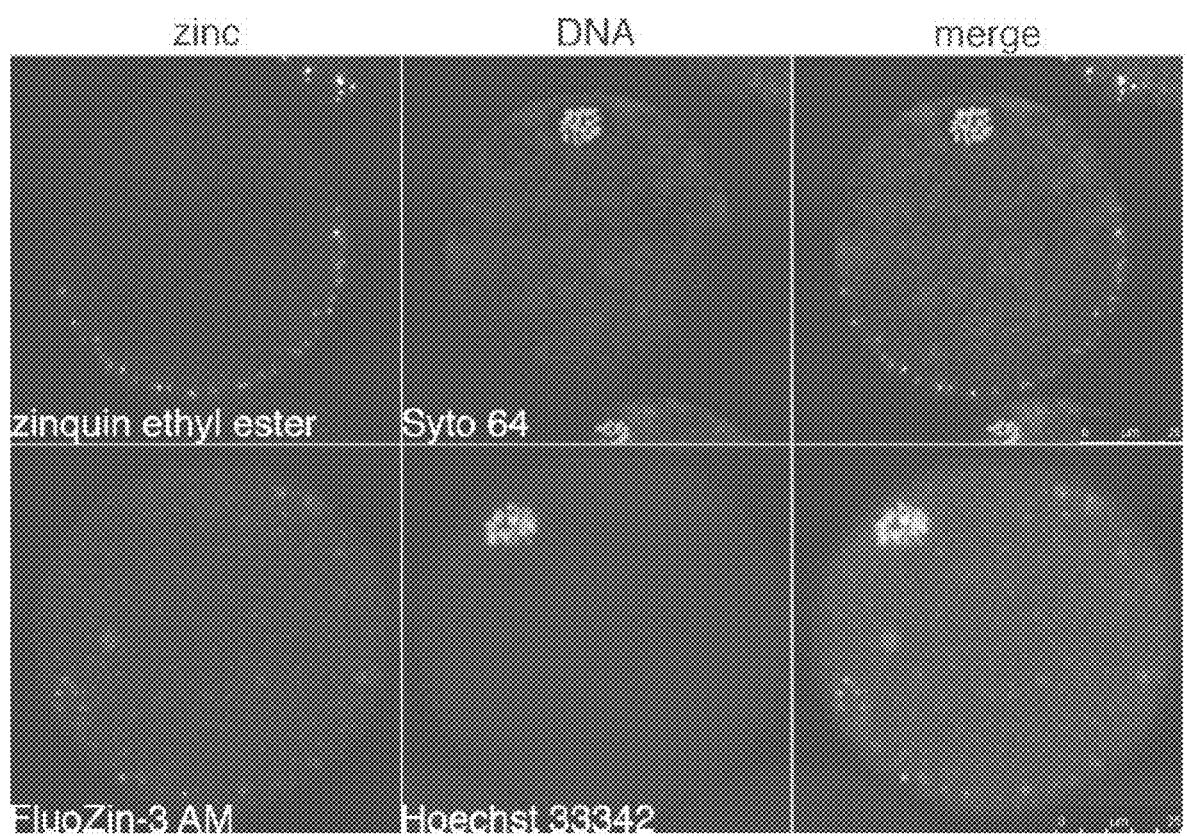
FIG. 8 shows optical sections from areas near the meiotic spindle (as detected by DNA markers Syto 64 and Hoechst 33342), selected from the complete confocal Z-series and projected to show the cortical localization of zinc-enriched vesicles as detected by two independent fluorophores, zinquin ethyl ester and FluoZin-3 AM. Merged images are also shown for clarity.

Experiments were conducted during development of embodiments of the present invention to determine whether the polarized pattern for total zinc correlated with the distribution of labile (or chelator-accessible) zinc in the egg. Two chemically distinct, zinc-selective fluorophores were used to visualize loosely bound zinc in live, unfertilized eggs. Projected images of confocal Z-stack series revealed that zinc fluorescence was concentrated away from the meiotic spindle, which was marked with fluorescent DNA probes (SEE FIG. 5C-5H). This was also evident when analyzing the Z-series slice by slice, which clearly illustrated higher cortical localization of zinc relative to the cytoplasm (SEE FIG. 8). Furthermore, zinc was present in distinct intracellular compartments as indicated by punctate foci of fluorescence. This pattern was independent of the molecular properties of the zinc probe: both zinquin ethyl ester (SEE FIG. 5C) and FluoZin-3 AM (SEE FIG. 5F) yielded the same general pattern wherein a majority of the foci have a peripheral localization. These probes have pM values of 9.3 and 8.8, respectively, where pM (like pH) reflects the log of the free ion concentration (Qian & Kennedy. (2002) J Am Chem Soc 124, 776-8.; Fahrni & O'Halloran. (1999) J Am Chem Soc 121, 11448-11458.; herein incorporated by reference in their entireties). Given that the pM value of zinc-binding metalloproteins are significantly higher, for example, carbonic anhydrase has a pM value of 12.4 (Fahrni & O'Halloran. (1999) J Am Chem Soc 121, 11448-11458.; herein incorporated by reference in its entirety), it is unlikely that the probes are detecting zinc tightly bound to metalloproteins. Rather, the probes are delineating compartments with elevated concentrations of free or weakly bound zinc ions. In addition to their punctate distribution, the pools of chelator-accessible zinc were concentrated towards the vegetal pole and away from the meiotic spindle, whose location was marked with live-cell nuclear stains Syto 64 (SEE FIG. 5D) or Hoechst 33342 (SEE FIG. 5G) as seen in the merged images (SEE FIGS. 5E and 5H). The polarized distribution detected both by the zinc fluorophores and by XFM corroborates a significant cortical compartmentalization of zinc in the egg. The polarized distribution of labile zinc mirrors the polarized release of zinc during the zinc sparks, indicating that some fraction of these zinc-enriched compartments act the source of the coordinated zinc release events, i.e., the zinc sparks.

Figure 9A:
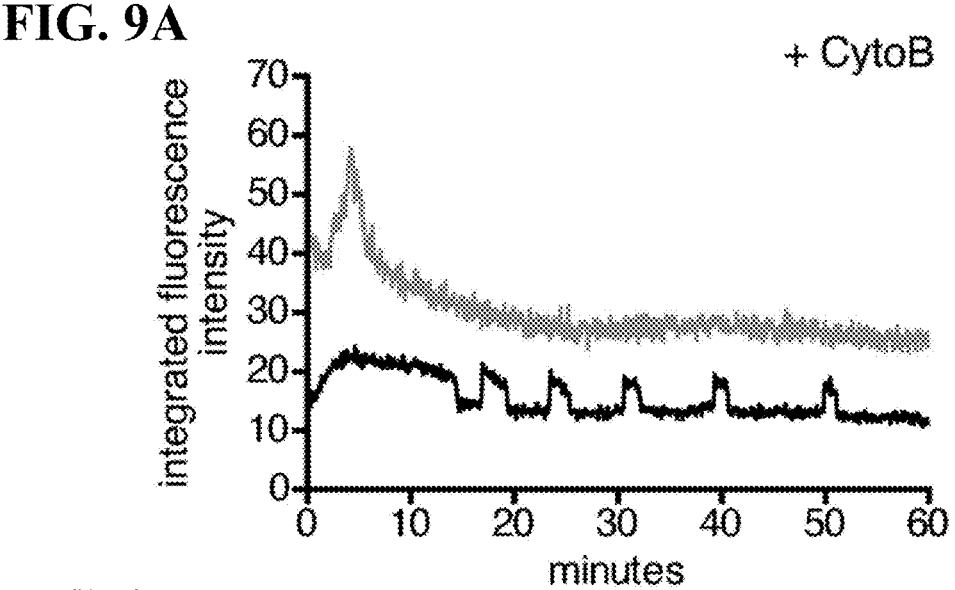
FIGS. 9a-9b show exocytosis was inhibited by treating eggs with cytochalasin B prior to activation with strontium chloride. Cytochalasin B did not affect the calcium oscillations (a) but blocked all but the first zinc spark in most cases (b).
Figure 9B:
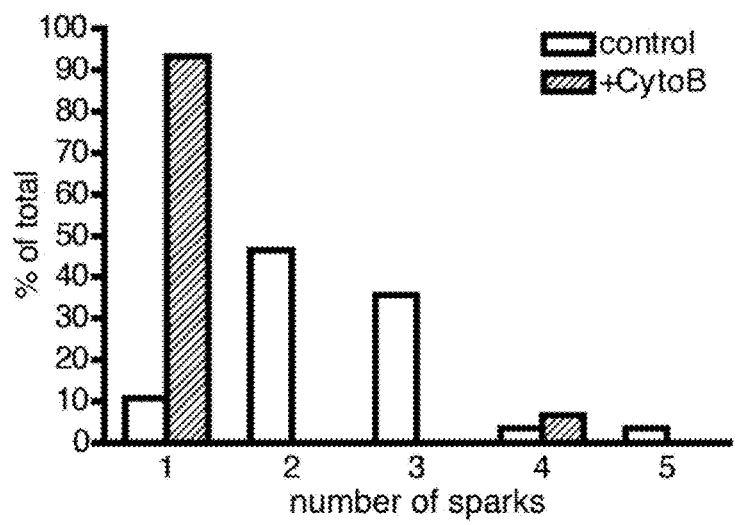

The polarization of the zinc-enriched vesicles mirrors that of the cortical granules (CG), which are exocytic vesicles that participate in the cortical reaction, which involves the hardening of the zona pellucida to establish a block to polyspermy at fertilization (Ducibella. (1996) Hum Reprod Update 2, 29-42.; herein incorporated by reference in its entirety). To inhibit exocytosis, eggs were treated with cytochalasin B (CytoB), an agent that disrupts actin reorganization and has previously been shown to disrupt CG exocytosis in mouse and hamster eggs (Tahara et al. (1996) Am J Physiol 270, C1354-61.; Zhang et al. (2005) Hum Reprod 20, 3053-61.; incorporated herein by reference in its entirety). CytoB-treated eggs still undergo normal calcium oscillations upon activation but only exhibit a single zinc spark concomitantly with the first calcium transient (SEE FIG. 9). In most cases, subsequent sparks were inhibited (SEE FIG. 9). Experiments conducted during development of embodiments of the present invention indicate that zinc-containing vesicles are pre-fused with the egg membrane, allowing the first spark to occur even in the presence of CytoB. This type of phenomenon has been described for cortical granules in the sea urchin egg, where one subset of CGs are in a hemifused state prior to activation21.

To determine whether the zinc sparks participate in zona hardening like the cortical reaction, a zinc-insufficient egg model that was obtained by treating oocytes with the heavy metal chelator TPEN during in vitro maturation was used (Kim et al. (2010) Nat Chem Biol 6, 674-81.; herein incorporated by reference in its entirety). These eggs did not undergo zinc sparks, even when activated in the same dish as control eggs. Zinc-insufficient eggs fertilize at rates comparable to control eggs. Additionally, zinc-insufficient eggs form the normal number of pronuclei, as indicated by the presence of only one male and one female pronucleus (Kim et al. (2010) Nat Chem Biol 6, 674-81.; herein incorporated by reference in its entirety). Therefore, there is no evidence to suggest that the zinc sparks participate in the block to polyspermy.

EXAMPLE 5

Meiotic Resumption at Egg Activation is Dependent on the Zinc Sparks

Figure 10:
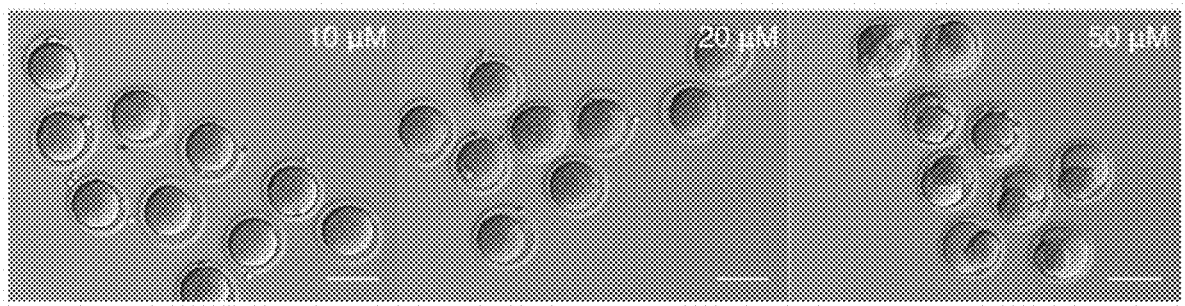
FIG. 10 shows dose response of unfertilized eggs to increasing concentrations of zinc pyrithione (ZnPT). Unfertilized eggs were treated with 10, 20, or 50 µM ZnPT for 15 min. A clear cytotoxic phenotype was only seen at 50 µM concentration. Thus, the effects of pyrithione are significantly below the threshold concentration (i.e., 500% lower) and do not involve cytotoxicity, as pyrithione was used at a minimum concentration (10 µM) and for a shorter duration (10 min).

The zinc-insufficient egg model revealed a critical function for zinc in the proper establishment of cell cycle arrest in the mature egg (Kim et al. (2010) Nat Chem Biol 6, 674-81.; herein incorporated by reference in its entirety), which was supported by the observation that chelation of zinc initiated egg activation (Suzuki et al. (2010) Development 137, 2659-2669; herein incorporated by reference in its entirety). Experiments were conducted during development of embodiments of the present invention to determine whether a decrease in bioavailable zinc was necessary to permit downstream developmental events upon egg activation. To address this possibility, activated eggs were treated with zinc pyrithione (ZnPT), a zinc ionophore that elevates the intracellular free zinc content of mammalian cells (Taki. (2004) J Am Chem Soc 126, 712-3.; herein incorporated by reference in its entirety). First, a titration was performed on unfertilized eggs and did not observe cytotoxic effects until concentrations of ZnPT reached 50 µM (SEE FIG. 10). To minimize such cytotoxic effects, a fivefold lower concentration of ZnPT (10 µM) was used for subsequent experiments. Eggs were subjected to a 10 min ZnPT treatment after the completion of the zinc sparks at 1.5 hours postactivation (hpa) (SEE FIG. 11A). Control (untreated) and ZnPT-treated eggs were then cultured until pronuclear formation was observed in the control group (6-8 hpa; SEE FIGS. 11B and 11C). Ninety percent of control eggs formed an organized pronucleus that was visible by brightfield (SEE FIG. 11B, arrowheads) and also by fluorescence (SEE FIG. 11D). F-actin was homogeneous around the cell (SEE FIG. 11E) and α-tubulin was compact in a spindle remnant (SEE FIG. 11F) between the egg and the second polar body (SEE FIG. 11G).

In contrast, only seventeen percent of ZnPT-treated eggs formed a pronucleus; the majority did not have a pronuclear structure that was clearly visible by brightfield (SEE FIG. 11C). In eighty-four percent of these eggs lacking a pronucleus, we noted the presence of aligned chromosomes (SEE FIG. 11H), instead of the membrane-enclosed nucleus observed in the control eggs.

Notably, an actin-enriched region in the ZnPT-treated eggs was also observed (SEE FIG. 11I, arrow) at the cortical region overlying the chromosomes (SEE FIG. 11J). This "actin cap" is a polarized feature thought to be unique to unfertilized eggs (Longo & Chen. (1985) Dev Biol 107, 382-94.; Duncan et al. (2005) Dev Biol 280, 38-47.; herein incorporated by reference in their entrireties). Most strikingly, the chromosomes and α-tubulin (SEE FIG. 11J) were organized into a metaphase-like spindle (SEE FIG. 11K), which resembled a freshly ovulated, MII-arrested egg (SEE FIG. 11L-O). It should be noted that only eggs with a clear second polar body were selected for ZnPT treatment; thus, the spindle configuration in ZnPT-treated activated eggs, while metaphase-like, is not that of metaphase II. An analogous metaphase-like spindle and arrest has been seen in parthenogenetically activated rodent eggs that receive insufficient activating stimulus: such cells complete meiosis II but stall at a so-called third metaphase (MIII) instead of progressing to interphase (Kubiak. (1989) Dev Biol 136, 537-45.; Zernicka-Goetz. (1991) Mol Reprod Dev 28, 169-76.; herein incorporated by reference in their entireties).

In the reverse of the zinc-loading experiment, the intracellular availability of zinc in the egg was decreased by continuous culture in the presence of 10 µM TPEN. After 8 hrs of culture, most control eggs maintained metaphase II arrest while those exposed to TPEN had a pronucleus-like structure at significantly higher rates (SEE FIG. 12). These complementary experiments support the finding that a significantly elevated zinc quota is associated with metaphase arrest and that the coordinated exocytosis of zinc upon egg activation relieves this arrest. Furthermore, these results also distinguish the intracellular target of the calcium-selective chelator BAPTA AM (SEE FIG. 4) from that of TPEN. BAPTA is also known to have a substantial affinity for zinc (Haugland., Handbook of fluorescent probes and research chemicals. 6th ed. Molecular Probes: Eugene, Oreg., 2001.; Grynkiewicz et al. (1985) *J Biol Chem* 260, 3440-50.; Stork & Li. (2006) *J Neurosci* 26, 10430-7.; herein incorporated by reference in their entireties). At the 10 µM concentration used in experiments conducted during development of embodiments of the present invention, BAPTA and TPEN had significantly different effects on egg physiology. This is illustrated by the fact that long-term exposure to BAPTA did not parthenogenetically activate eggs (SEE FIG. 4) but TPEN did (SEE FIG. 12). Under these conditions, BAPTA is scavenging intracellular free calcium and thereby blocking calcium oscillations. Taken together, the results support the finding that calcium oscillations initiate and are required for the programmed loss of cellular zinc via the zinc sparks and that in turn drives cell cycle resumption.

EXAMPLE 6

Zn-Responsive Probe Synthesis

Figure 14:
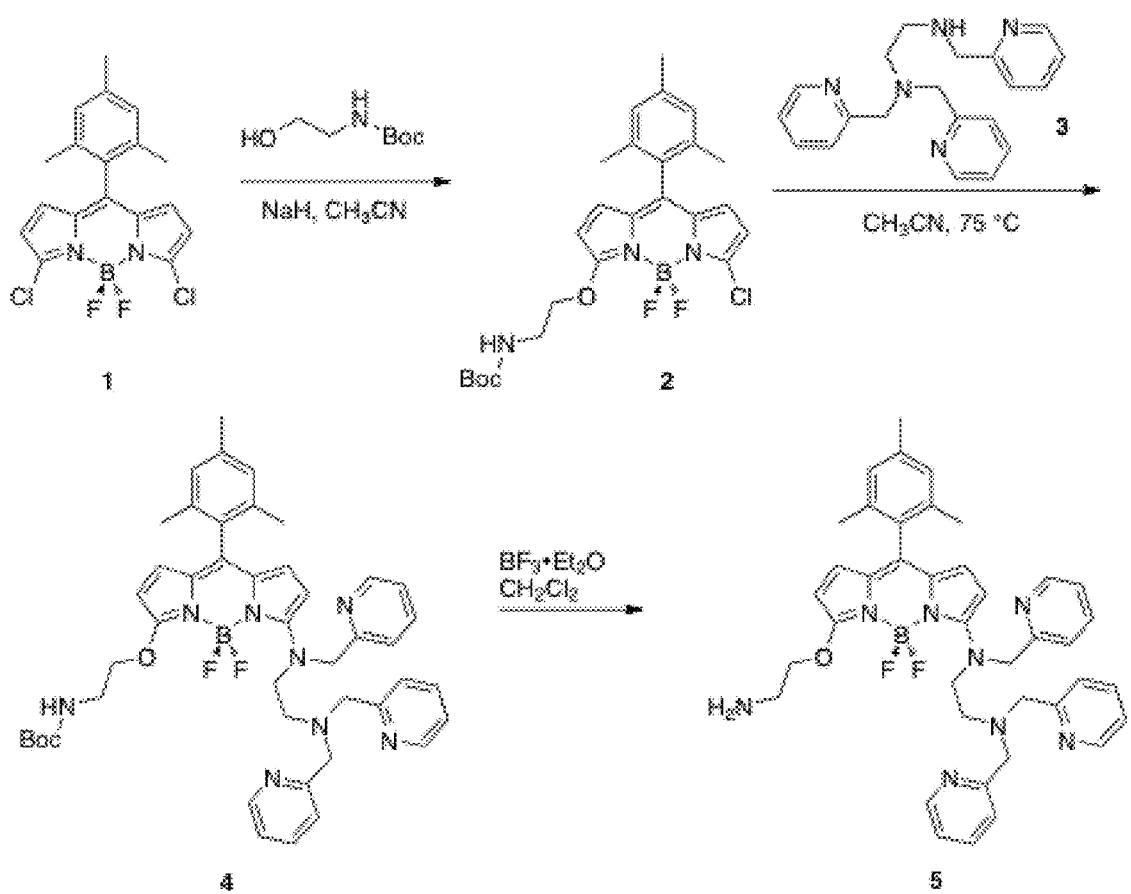
FIG. 14 shows a synthesis scheme for an exemplary Zn-responsive probe of the present invention.

Experiments were conducted during development of embodiments of the present invention to synthesize a Zn-responsive probe comprising: a Zn-chelating ligand containing five Zn-binding groups (three pyridyl groups and two tertiary amines), a BODIPY fluorophore that has excitation and emission wavelengths in the visible spectrum, an ethanol ether based linker, and an amine group to enable attachment to carboxylate-modified surfaces via amide coupling chemistries (SEE FIG. 13). The starting material, Compound 1, is synthesized according to literature procedures (Domaille et al. J. Am. Chem. Soc 2010, 132, 1194-1195.; herein incorporated by reference in its entirety). Compound 1 was combined with N-boc-ethanolamine and sodium hydride to yield compound 2. This was then heated in the presence of the Zn-binding group 3 to furnish compound 4. Finally, the Boc group was removed from compound 4 using borontrifluoride diethyletherate to yield amine-functionalized compound 5 (SEE FIG. 14). Experiments conducted during development of the present invention demonstrated that the probe synthesized in Example 6 undergoes alteration in its detectable signal (BODIPY fluorescence) upon binding of Zn to the Zn-chelating ligand.

EXAMPLE 7

ZincBY-1 Probe Synthesis

Figure 15A:
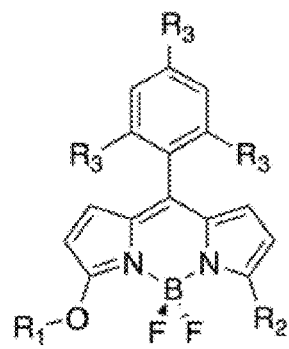
FIG. 15A shows a formula for an exemplary Zn-responsive probe.
Figure 15B:
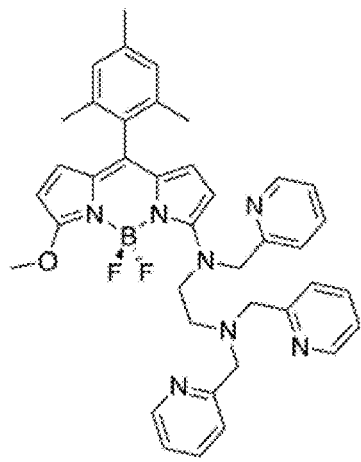
FIG. 15B shows the chemical structure of exemplary probe ZincBy-1.
Figure 15C:
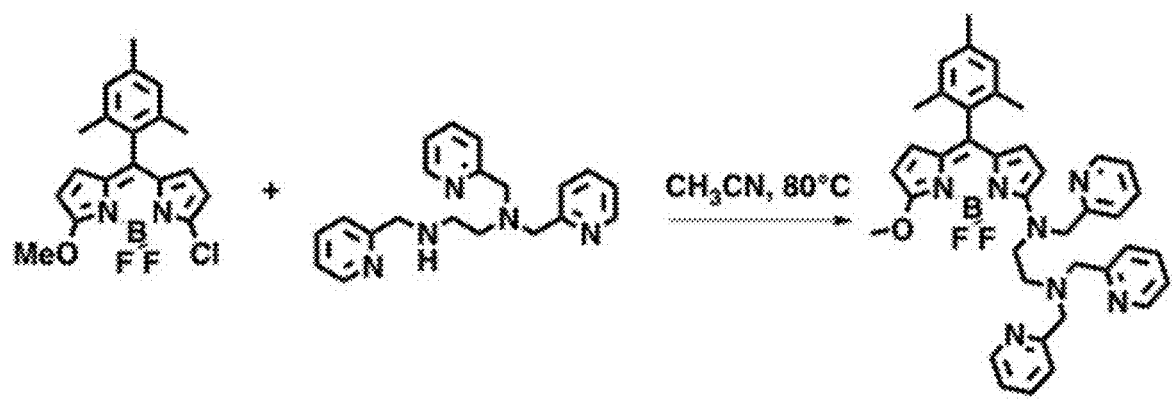
FIG. 15C shows a schematic of the synthesis scheme for ZincBy-1 described in Example 7 below.

This Example describes the synthesis of an exemplary probe called ZincBy-1, which is pictured in FIG. 15B. A schematic of this synthesis is shown in FIG. 15C. ZincBy-1 is readily synthesized in 70% yield from starting materials that have been previously reported (see, Domaille, et al. J. Am. Chem. Soc. 2010, 132, 1194-1195; and Hureau, et al. Inorg. Chem. 2008, 47, 9238-9247., both of which are herein incorporated by reference).

3-Chloro-5-methoxy-8-mesityl-BODIPY (32 mg, 0.085 mmol) and $N^1$-(pyridin-2-yl)-$N^2$,$N^2$-bis(pyridin-2-ylmethyl)ethane-1,2-diamine (57 mg, 0.17 mmol) were combined in 5 mL of dry CH3CN in an oven dried Schlenk flask under Na. The reaction was heated at 80° C. overnight. Following cooling and solvent removal, the product was purified by silica gel chromatography (0-5% CH$_3$OH in CH$_2$Cl2) to yield the pure product as a dark pink residue (40 mg, 70% yield). $^1$H NMR (CDCl$_3$, 500 MHz): δ 8.51 (1H, m), 8.48 (2H, m), 7.62 (3H, dq, J=2.0, 7.5 Hz), 7.53 (2H, d, J=8.0 Hz), 7.37 (1H, d, J=8.0 Hz), 7.15 (1H, m), 7.12 (2H, m), 6.89 (2H, s), 6.34 (1H, d, J=4.5), 6.10 (1H, d, J=4.0 Hz), 5.87 (1H, d, J=4.5 Hz), 5.61 (1H, d, J=4.0 Hz), 5.22 (2H, s), 3.96 (3H, s), 3.89 (4H, s), 3.86 (2H, m), 2.92 (2H, m), 2.33 (3H, s), 2.08 (6H, s). $^{13}$C NMR (CDCl$_3$, 125 MHz): δ 164.51, 164.27, 160.03, 156.42, 148.03, 147,58, 136.69, 136.39, 135.98, 131.91, 130.60, 129.37, 128,36, 126.37, 126.83, 124.37, 121.59, 121.56, 121.39, 121.15, 110.10, 106.20, 52.44, 30.92, 30.59, 29.96, 28.70, 21.70, 18.89, 13.14 ESI-MS MH$^+$ $C_{39}H_{41}BF_2N_7O^+$ calc. 672.6, found 672.3.

EXAMPLE 8

ZincBY-1 Probe Characterization

Figure 16:
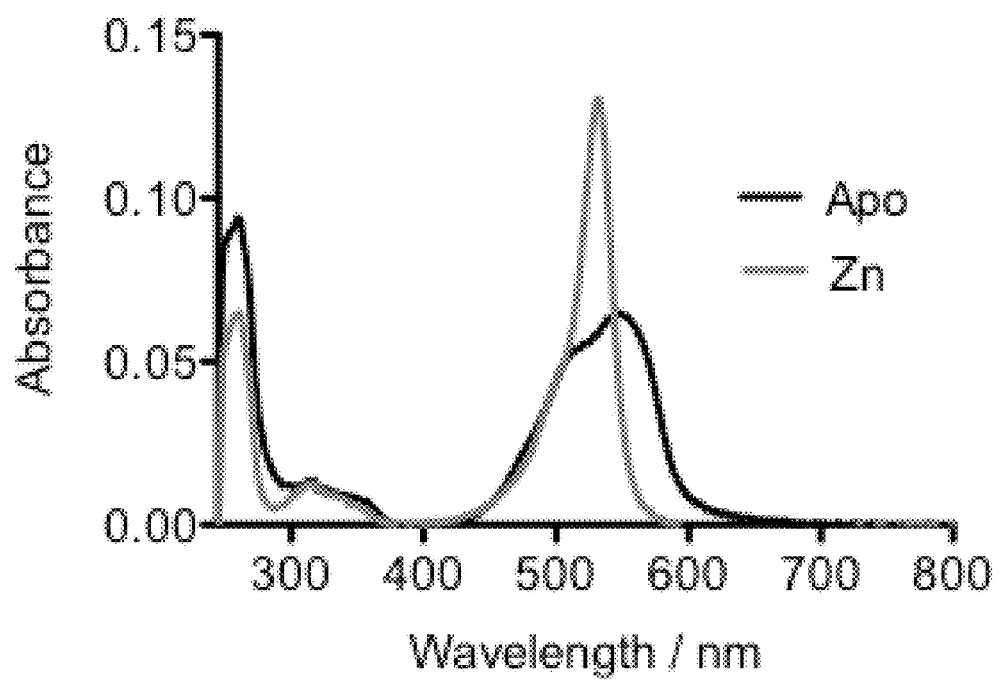
FIG. 16 shows an absorbance spectra of 5 µM ZincBY-1 in 50 mM HEPES, 0.1 M KNO$_3$, pH 7.2. "Apo" represents the absorbance spectrum in the absence of zinc binding and "Zn" represents the absorbance spectrum in the presence of 1 equiv of ZnSO$_4$.
Figure 17:
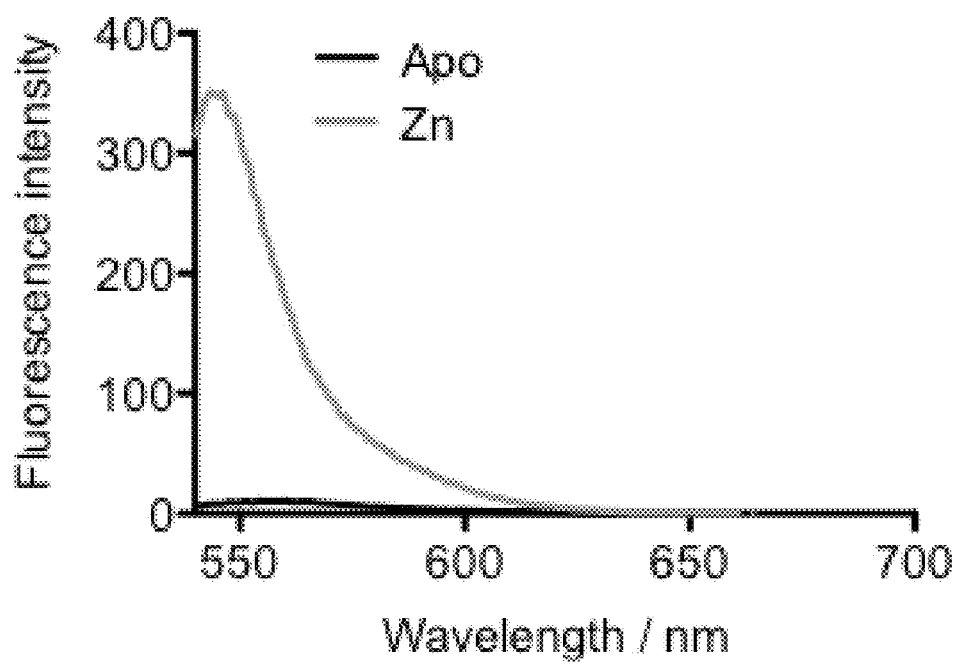
FIG. 17 shows fluorescence spectra of 5 µM ZincBY-1 in 50 mM HEPES, 0.1 M KNO$_3$, pH 7.2. "Apo" represents the fluorescence in the absence of zinc binding and "Zn" represents the fluorescence in the presence of 1 equiv of ZnSO$_4$. 530 nm light was used for excitation and the maximum fluorescence occurs at 543 nm.

This Example describes the characterization of the ZincBy-1 probe, which is shown in FIG. 15B. ZincBY-1 has excellent in vitro spectroscopic properties and can be used, for example, in live cells at nanomolar concentrations (see below). ZincBY-1 was characterized spectroscopically. Solutions of 5 µM of ZincBY-1 in 50 mM HEPES, 0.1 M KNO$_3$, pH 7.2 were analyzed for their absorbance and fluorescence properties (FIGS. 16 and 17). Absorbsbance properties of the apo- and zinc-bound forms of the probe reveal absorbance in the 500 to 600 nm range, which is typical for BODIPY-based sensors (FIG. 16). The extinction coefficient for the apo form is 12,000 cm$^{-1}$M$^{-1}$ and for the Zn-bound form is 28,000 cm$^{-1}$M$^{-1}$. Fluorescence characterization (FIG. 17) with an excitation wavelength of 530 nm revealed minimal fluorescence in the Apo form (quantum yield=0.02). Upon addition of 1 equiv ZnSO$_4$, fluorescence at 543 nm increases substantially, with a quantum yield of 0.46. Taken together, these data reveal a ~50-fold fluorescence turn-on for Zn, which is comparable with the state-of-the-art commercially available probe FluoZin-3 (Gee, et al. J. Am. Chem. Soc. 2002, 124, 776-778, which is herein incorporated by reference), which has a 80-fold turn on.

Figure 18:
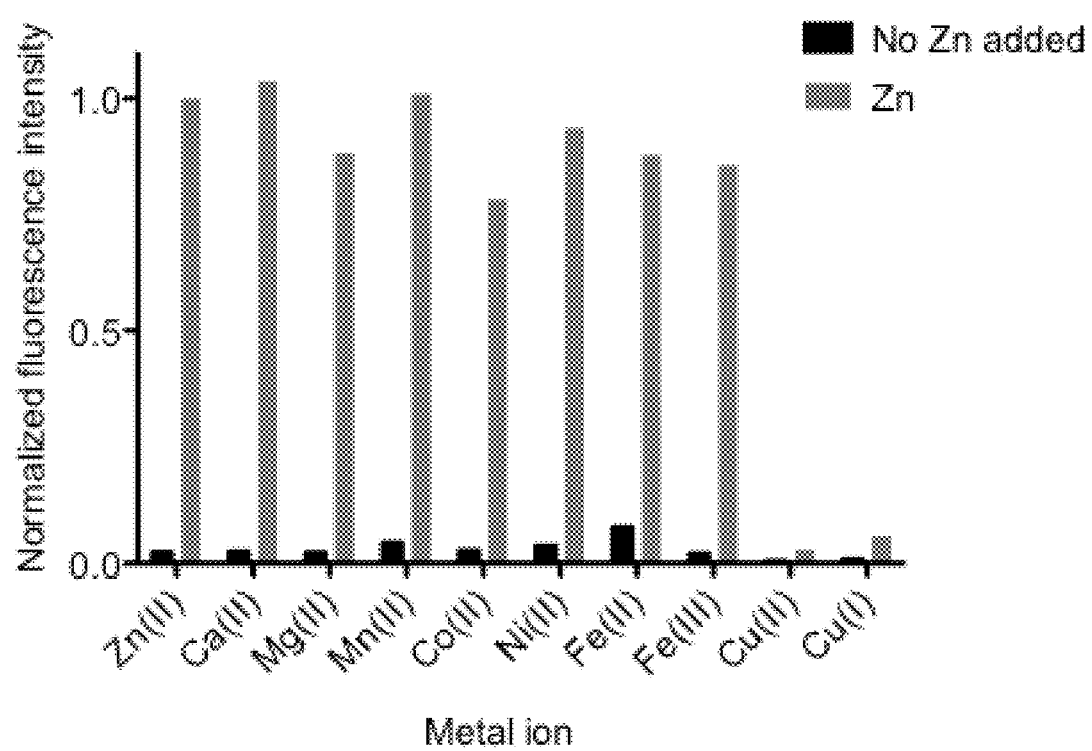
FIG. 18 shows the metal ion selectivity of ZincBY-1. Black bars represent ZincBY-1 fluorescence in the absence of zinc but in the presence of Ca (5 mM), Mg (5 mM), Mn, Co, Fe, and Cu (all 10 µM). Green bars represent the fluorescence in the presence of 1 equiv of zinc and Ca (5 mM), Mg (5 mM), Mn, Co, Fe, and Cu (all 10 µM).

ZincBY-1 is selective for Zn$^{2+}$ over a range of metal ions including Ca$^{2+}$, Mg$^{2+}$, Mn$^{2+}$, Fe$^{2+}$, Fe$^{3+}$, Co$^{2+}$, Ni$^{2+}$, Cu$^{2+}$, and Cu$^+$ (FIG. 18). In the absence of Zn, none of these metal ions induce an increase in ZincBY-1 fluorescence. In the presence of Ca$^{2+}$, Mg$^{2+}$, Mn$^{2+}$, Fe$^{2+}$, Fe$^{3+}$, Co$^{2+}$, and Ni$^{2+}$, ZincBY-1 is still capable of detecting Zn as addition of Zn induces a fluorescence increase. In the presence of Cu$^{2-}$ and Cu$^+$, however, ZincBY-1 does not respond to Zn addition, indicating that Cu$^{2+}$ and Cu$^+$ bind ZincBY-1 more tightly than Zn$^{2+}$ but quench ZincBY-1-based fluorescence. In a cellular context, Zn is present in ~10× excess of Cu, and thus, interference from Cu is not expected in cells.

Figure 19:
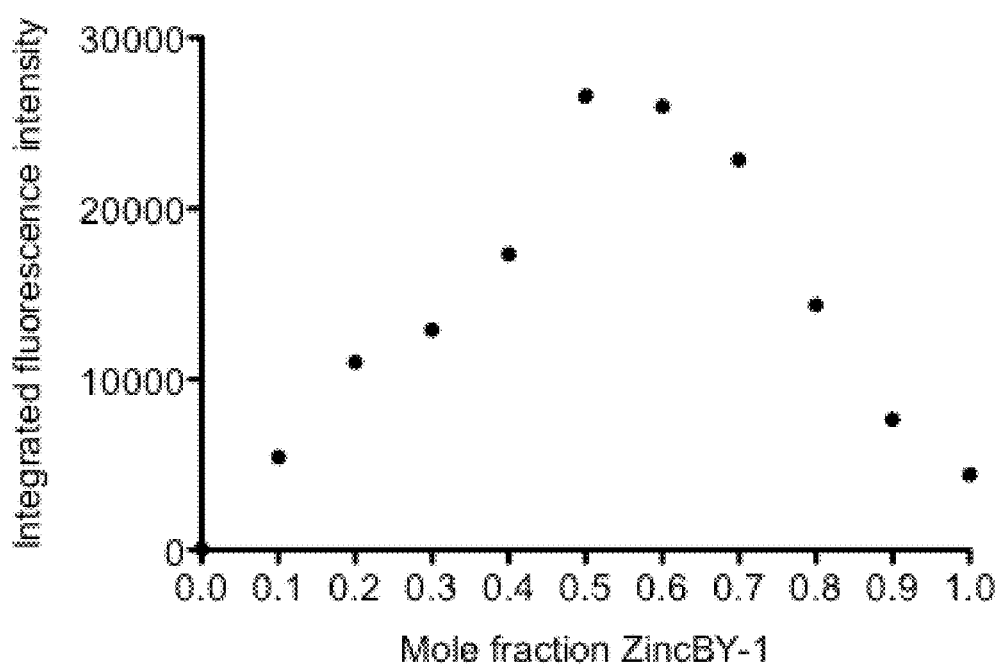
FIG. 19 shows a job plot of ZincBY-1, shown as a plot of mole fraction of ZincBY-1 vs. fluorescence intensity. The sum of the concentrations of ZincBY-1 and ZnSO$_4$ was held constant at 10 µM. The maximum at 0.5 molefraction supports a 1:1 ZincBY-1/Zn binding ratio.
Figure 20:
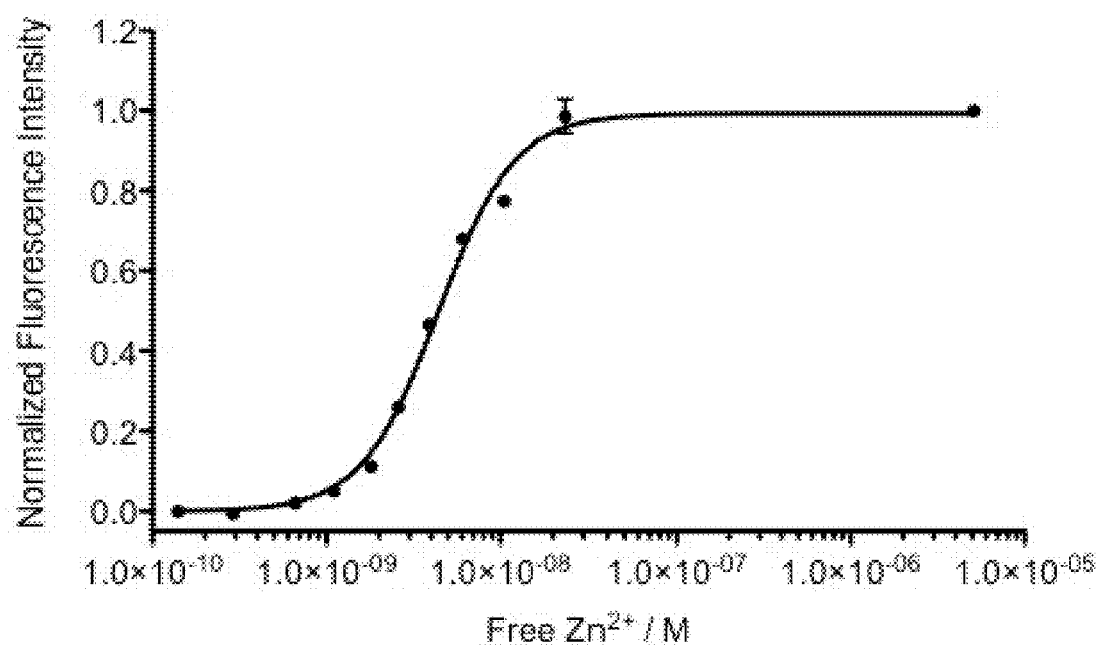
FIG. 20 shows a determination of ZincBY-1 dissociation constant ($K_D$). ZincBY-1 fluorescence was measured in the presence of EGTA-buffered solution of $Zn^{2+}$. Data was fit to a one-site binding model and yielded a $K_D=4.4\times10^{-9}$ M with a Hill coefficient of ~2.
Figure 21:
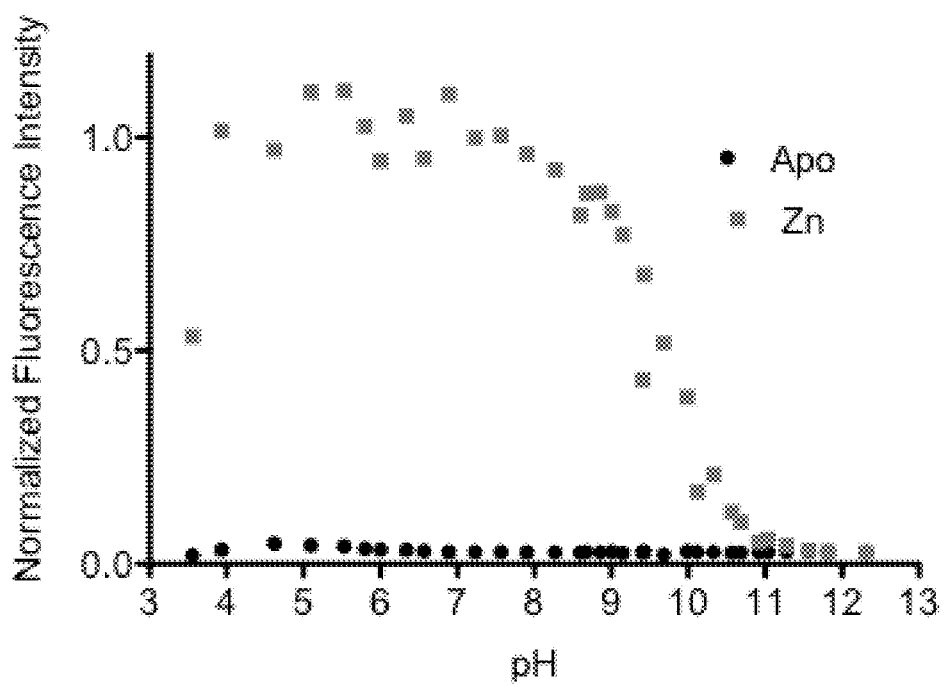
FIG. 21 shows the pH sensitivity of ZincBY-1. Normalized fluorescence intensity of ZincBY-1 in the absence (Apo) and presence (Zn) of zinc at various pH values. Little change in fluorescence is observed for the Apo probe over the range of pH values. Fluorescence from the Zn-bound probe is largely unchanged within the physiologically relevant pH range (pH 4-7).
Figure 23A:
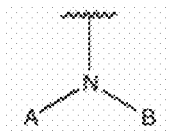
FIG. 23A shows exemplary formula for a Zn binding group.
Figure 23B:
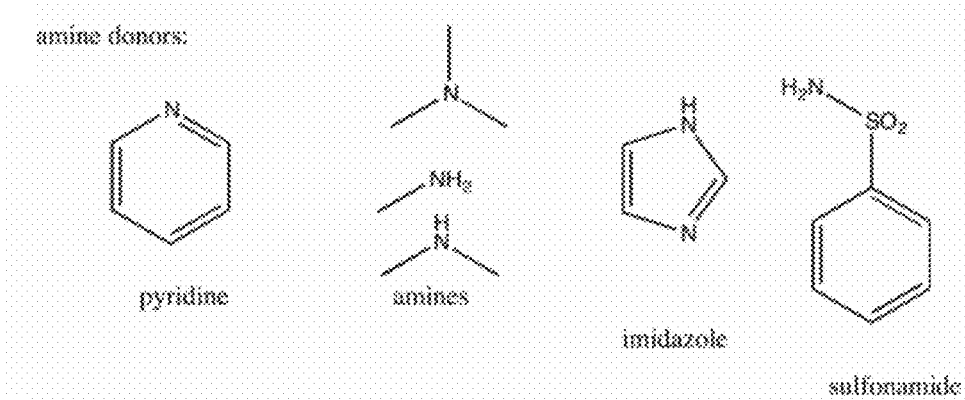
FIG. 23B shows exemplary amino donor moieties that could be used for, or as part of, A and/or B in the formula shown in FIG. 23A.
Figure 23C:
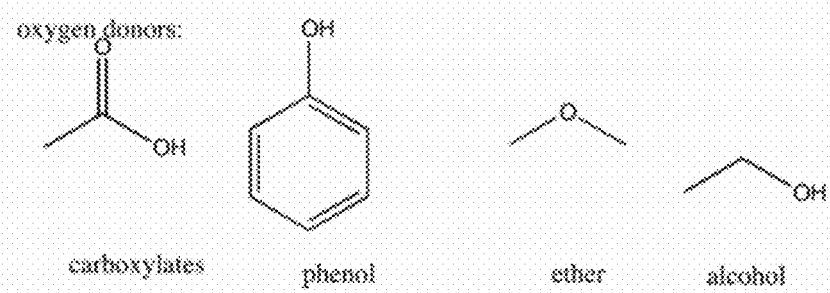
FIG. 23C shows exemplary oxygen donor moieties that could be used for, or as part of, A and/or B in the formula shown in FIG. 23A.
Figure 23D:
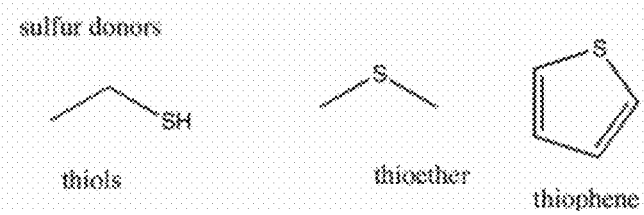
FIG. 23D shows exemplary sulfur donor moieties that could be used for, or as part of, A and/or B in the formula shown in FIG. 23A.

Zn binding of ZincBY-1 occurs in a 1:1 fashion as is demonstrated by the Job plot in FIG. 19. In these experiments, the combined ZincBY-1 and Zn concentration is held constant, but the proportions of the two components are varied. Maximum signal is observed at 0.5 mole fraction of both components, consistent with a 1:1 binding stoichiometry. ZincBY-1 binds zinc with nanomolar affinity as is shown in experiments where free Zn is buffered by EGTA (FIG. 20). The data is fitted to a curve that corresponds to $K_d$=4.4 nM, with a Hill slope of ~2. In the absence of zinc, ZincBY-1 displays constant fluorescence over a range of pH values (pH 3.5 to 12.2, FIG. 21). The zinc response of ZincBY-1 is robust over a pH range of pH 4 to 8, which matches well with the biologically relevant pH range.

Following in vitro characterization of ZincBY-1, the probe was tested in live MII mouse eggs. Live MII eggs were incubated in 50 nM ZincBY-1 and 0.1 mg/mL Hoechst for 10 minutes and transferred to an imaging dish. FIG. 22 depicts a confocal z-stack of an MII egg, with green representing ZincBY-1 fluorescence (indicates the presence of Zn) and blue represents Hoechst fluorescence (labels DNA). In this context, 50 nM ZincBY-1 is capable of labeling zinc-rich vesicles inside the cell.

All publications and patents mentioned in the present application and/or listed below are herein incorporated by reference. Various modification, recombination, and variation of the described features and embodiments will be apparent to those skilled in the art without departing from the scope and spirit of the invention. Although specific embodiments have been described, it should be understood that the invention as claimed should not be unduly limited to such specific embodiments. Indeed, various modifications of the described modes and embodiments that are obvious to those skilled in the relevant fields are intended to be within the scope of the following claims.

REFERENCES

1. Berridge, M. J.; Bootman, M. D.; Roderick, H. L. (2003) Calcium signalling: dynamics, homeostasis and remodelling, *Nat Rev Mol Cell Biol* 4, 517-29.
2. Lawrence, Y.; Whitaker, M.; Swann, K. (1997) Sperm-egg fusion is the prelude to the initial Ca2+ increase at fertilization in the mouse, *Development* 124, 233-41.
3. Ozil, J. P.; Banrezes, B.; Toth, S.; Pan, H.; Schultz, R. M. (2006) Ca2+ oscillatory pattern in fertilized mouse eggs affects gene expression and development to term, *Dev Biol* 300, 534-44.
4. Ducibella, T.; Huneau, D.; Angelichio, E.; Xu, Z.; Schultz, R. M.; Kopf, G. S.; Fissore, R.; Madoux, S.; Ozil, J. P. (2002) Egg-to-embryo transition is driven by differential responses to Ca(2+) oscillation number, *Dev Biol* 250, 280-91.
5. Toth, S.; Huneau, D.; Banrezes, B.; Ozil, J. P. (2006) Egg activation is the result of calcium signal summation in the mouse, *Reproduction* 131, 27-34.
6. Kline, D.; Kline, J. T. (1992) Repetitive calcium transients and the role of calcium in exocytosis and cell cycle activation in the mouse egg, *Dev Biol* 149, 80-9.
7. Tahara, M.; Tasaka, K.; Masumoto, N.; Mammoto, A.; Ikebuchi, Y.; Miyake, A. (1996) Dynamics of cortical granule exocytosis at fertilization in living mouse eggs, *Am J Physiol* 270, C1354-61.
8. Liu, J.; Mailer, J. L. (2005) Calcium elevation at fertilization coordinates phosphorylation of XErp1/Emi2 by Plx1 and CaMK II to release metaphase arrest by cytostatic factor, *Curr Biol* 15, 1458-68.
9. Madgwick, S.; Hansen, D. V.; Levasseur, M.; Jackson, P. K.; Jones, K. T. (2006) Mouse Emi2 is required to enter meiosis II by reestablishing cyclin B1 during interkinesis, *J Cell Biol* 174, 791-801.
10. Battaglia, D. E.; Gaddum-Rosse, P. (1987) Influence of the calcium ionophore A23187 on rat egg behavior and cortical F-actin, *Gamete Res* 18, 141-52.
11. Ozil, J. P. (1990) The parthenogenetic development of rabbit oocytes after repetitive pulsatile electrical stimulation, *Development* 109,117-27.
12. Zhang, D.; Pan, L.; Yang, L. H.; He, X. K.; Huang, X. Y.; Sun, F. Z. (2005) Strontium promotes calcium oscillations in mouse meiotic oocytes and early embryos through InsP3 receptors, and requires activation of phospholipase and the synergistic action of InsP3, *Hum Reprod* 20, 3053-61.
13. Tingen, C.; Rodriguez, S.; Campo-Engelstein, L.; Woodruff, T. K. (2010) Research funding. Politics and parthenotes, *Science* 330, 453.
14. Kim, A. M.; Vogt, S.; O'Halloran, T. V.; Woodruff, T. K. (2010) Zinc availability regulates exit from meiosis in maturing mammalian oocytes, *Nat Chem Biol* 6, 674-81.
15. Bernhardt, M. L.; Kim, A. M.; O'Halloran, T. V.; Woodruff, T. K. (2010) Zinc requirement during meiosis I-meiosis II transition in mouse oocytes is independent of the MOSMAPK pathway, *Biol Reprod published ahead of print Nov.* 10, 2010.
16. Gee, K. R.; Zhou, Z. L.; Qian, W. J.; Kennedy, R. (2002) Detection and imaging of zinc secretion from pancreatic beta-cells using a new fluorescent zinc indicator, *J Am Chem Soc* 124, 776-8.
17. Markoulaki, S.; Matson, S.; Abbott, A. L.; Ducibella, T. (2003) Oscillatory CaMKII activity in mouse egg activation, *Dev Biol* 258, 464-74.
18. Fahrni, C. J.; O'Halloran, T. V. (1999) Aqueous coordination chemistry of quinolinebased fluorescence probes for the biological chemistry of zinc, *J Am Chem Soc* 121, 11448-11458.
19. Ducibella, T. (1996) The cortical reaction and development of activation competence in mammalian oocytes, *Hum Reprod Update* 2, 29-42.
20. DiMaggio, A. J., Jr.; Lonergan, T. A.; Stewart-Savage, J. (1997) Cortical granule exocytosis in hamster eggs requires microfilaments, *Mol Reprod Dev* 47, 334-40.
21. Wong, J. L.; Koppel, D. E.; Cowan, A. E.; Wessel, G. M. (2007) Membrane hemifusion is a stable intermediate of exocytosis, *Dev Cell* 12, 653-9.
22. Suzuki, T.; Yoshida, N.; Suzuki, E.; Okuda, E.; Perry, A. C. (2010) Full-term mouse development by abolishing Zn2+-dependent metaphase II arrest without Ca2+ release, *Development* 137, 2659-2669.
23. Taki, M.; Wolford, J. L.; O'Halloran, T. V. (2004) Emission ratiometric imaging of intracellular zinc: design of a benzoxazole fluorescent sensor and its application in two-photon microscopy, *J Am Chem Soc* 126, 712-3.
24. Longo, F. J.; Chen, D. Y. (1985) Development of cortical polarity in mouse eggs: involvement of the meiotic apparatus, *Dev Biol* 107, 382-94.
25. Duncan, F. E.; Moss, S. B.; Schultz, R. M.; Williams, C. J. (2005) PAR-3 defines a central subdomain of the cortical actin cap in mouse eggs, *Dev Biol* 280, 38-47.
26. Kubiak, J. Z. (1989) Mouse oocytes gradually develop the capacity for activation during the metaphase II arrest, *Dev Biol* 136, 537-45.
27. Zernicka-Goetz, M. (1991) Spontaneous and induced activation of rat oocytes, *Mol Reprod Dev* 28, 169-76.
28. Haugland, H. P., Handbook of fluorescent probes and research chemicals. 6th ed.; Molecular Probes: Eugene, Oreg., 2001.
29. Grynkiewicz, G.; Poenie, M.; Tsien, R. Y. (1985) A new generation of Ca2+ indicators with greatly improved fluorescence properties, *J Biol Chem* 260, 3440-50.
30. Stork, C. J.; Li, Y. V. (2006) Intracellular zinc elevation measured with a "calciumspecific" indicator during ischemia and reperfusion in rat hippocampus: a question on calcium overload, *J Neurosci* 26, 10430-7.
31. Shoji, S.; Yoshida, N.; Amanai, M.; Ohgishi, M.; Fukui, T.; Fujimoto, S.; Nakano, Y.; Kajikawa, E.; Perry, A. C.

(2006) Mammalian Emi2 mediates cytostatic arrest and transduces the signal for meiotic exit via Cdc20, *EMBO J* 25, 834-45.

32. Suzuki, T.; Suzuki, E.; Yoshida, N.; Kubo, A.; Li, H.; Okuda, E.; Amanai, M.; Perry, A. C. (2010) Mouse Emi2 as a distinctive regulatory hub in second meiotic metaphase, *Development* 137,3281-91.

33. Xu, M.; West, E.; Shea, L. D.; Woodruff, T. K. (2006) Identification of a stage-specific permissive in vitro culture environment for follicle growth and oocyte development, *Biol Reprod* 75, 916-23.34. Kramer, C. Y. (1956) Extension of multiple range tests to group means with unequalnumbers of replications, *Biometrics* 12, 309-310.

We claim:

1. A method of non-invasively detecting Zn release by a methaphase-II-arrested oocyte comprising:
    a) contacting a sample comprising a metaphase-II-arrested oocyte with a composition comprising a Zn-responsive probe,
    wherein said Zn-responsive probe has the following chemical structure:

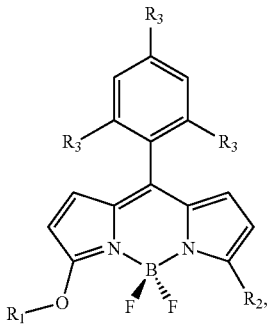

wherein each of said $R_{3s}$ are individually selected from: H, $CH_3$, an alkyl group, an O-alkyl group, an N-alkyl group, a linker group, an attachment group, and a linker group attached to an attachment group;

wherein said $R_1$ is selected from: H, $CH_3$, an alkyl group, a linker group, an attachment group, and a linker group attached to an attachment group; and wherein said $R_2$ is a Zn binding group, wherein said Zn-responsive probe is present in said composition at a concentration between $1 \times 10^{-5}$ M and $1 \times 10^{-9}$ M;

b) contacting said sample with sperm; and c) detecting the signal emitted by the Zn-responsive probe over time, wherein detecting said signal over time comprises capturing a time lapse series of images of the fluorescence level in the extracellular area surrounding said metaphase-II arrested oocyte such that at least one zinc spark is detected.

2. The method of claim 1, wherein the Zn-responsive probe is attached to a surface.

3. The method of claim 1, wherein the concentration of said Zn-responsive probe is between $1 \times 10^{-7}$ and $1 \times 10^{-8}$ M.

4. The method of claim 1, wherein said correlating said signal comprises correlating the significant increase in extracellular Zn concentration to fertilization of the oocyte by the sperm.

5. The method of claim 4, further comprising removing the oocyte from the Zn-responsive probe, and implanting the fertilized oocyte into a subject.

* * * * *